(12) United States Patent
Susi

(10) Patent No.: US 11,268,506 B2
(45) Date of Patent: Mar. 8, 2022

(54) FLUID PUMPS FOR USE IN MRI ENVIRONMENT

(71) Applicant: IRADIMED CORPORATION, Winter Springs, FL (US)

(72) Inventor: Roger E. Susi, Winter Park, FL (US)

(73) Assignee: IRADIMED CORPORATION, Winter Springs, FL (US)

( * ) Notice: Subject to any disclaimer, the term of this patent is extended or adjusted under 35 U.S.C. 154(b) by 0 days.

(21) Appl. No.: 15/852,680

(22) Filed: Dec. 22, 2017

(65) Prior Publication Data
US 2019/0192017 A1    Jun. 27, 2019

(51) Int. Cl.
| | |
|---|---|
| F04B 43/04 | (2006.01) |
| A61B 5/0235 | (2006.01) |
| A61B 5/022 | (2006.01) |
| F04B 49/06 | (2006.01) |
| F04B 43/00 | (2006.01) |
| A61B 5/021 | (2006.01) |
| F04B 53/10 | (2006.01) |
| F04B 49/20 | (2006.01) |
| A61B 5/055 | (2006.01) |

(52) U.S. Cl.
CPC ............ *F04B 43/046* (2013.01); *A61B 5/022* (2013.01); *A61B 5/0235* (2013.01); *A61B 5/02141* (2013.01); *A61B 5/02233* (2013.01); *F04B 43/00* (2013.01); *F04B 49/06* (2013.01); *A61B 5/055* (2013.01); *F04B 49/20* (2013.01); *F04B 53/10* (2013.01)

(58) Field of Classification Search
CPC ... A61B 5/02233; A61B 5/0235; A61B 5/055; A61B 5/022; A61B 5/02141; F04B 43/046; F04B 49/06; F04B 49/20; F04B 53/10; F04B 43/04; F04B 43/02; F04B 43/00

See application file for complete search history.

(56) References Cited

U.S. PATENT DOCUMENTS

| | | | |
|---|---|---|---|
| 2,696,963 | A | 12/1954 | Shepherd |
| 4,221,224 | A | 9/1980 | Clark |
| 4,284,996 | A | 8/1981 | Greve |

(Continued)

FOREIGN PATENT DOCUMENTS

| | | |
|---|---|---|
| DE | 19714711 A1 | 10/1998 |
| EP | 0 447 985 A | 9/1991 |

(Continued)

OTHER PUBLICATIONS

Sashida, Toshiiku et al., An Introduction to Ultrasonic Motors, Oxford Science Publications, 1993, Selected Pages, 90 pages total.

(Continued)

*Primary Examiner* — Tse W Chen
*Assistant Examiner* — Avery M Foley
(74) *Attorney, Agent, or Firm* — Knobbe Martens Olson & Bear LLP

(57) ABSTRACT

Embodiments of fluid pumps configured for use in a magnetic resonance imaging environment are disclosed. The pumps may include piezoelectric driven pumping mechanisms or ultrasonic motor driven pumping mechanisms. The pumps may be configured to pump fluid such as air or liquid. The pumps may be incorporated in a multi-parameter patient monitoring system.

14 Claims, 12 Drawing Sheets

(56) References Cited

U.S. PATENT DOCUMENTS

| | | |
|---|---|---|
| 4,344,743 A | 8/1982 | Bessman et al. |
| 4,457,751 A | 7/1984 | Rodler |
| 4,460,358 A | 7/1984 | Somerville et al. |
| 4,564,812 A | 1/1986 | Van Dijk |
| 4,689,043 A | 8/1987 | Bisha |
| 4,798,590 A | 1/1989 | O'Leary |
| 4,833,379 A | 5/1989 | Kaibel et al. |
| 4,853,579 A | 8/1989 | Kawasaki et al. |
| 4,857,048 A | 8/1989 | Simons et al. |
| 4,888,514 A | 12/1989 | Takahashi et al. |
| 5,017,192 A | 5/1991 | Dodge et al. |
| 5,021,700 A | 6/1991 | Takahashi et al. |
| 5,041,132 A | 8/1991 | Miyata |
| 5,059,173 A | 10/1991 | Sacco |
| 5,172,023 A | 2/1992 | Kawai et al. |
| 5,097,829 A | 3/1992 | Quisenberry |
| 5,130,619 A | 7/1992 | Izuno |
| 5,149,030 A | 9/1992 | Cockrill |
| 5,181,910 A | 1/1993 | Scanlon |
| 5,290,239 A | 3/1994 | Classey et al. |
| 5,298,828 A | 3/1994 | Radovanovich |
| 5,357,827 A | 10/1994 | Natwick et al. |
| 5,401,256 A | 3/1995 | Stone et al. |
| 5,437,635 A | 8/1995 | Fields et al. |
| 5,466,932 A * | 11/1995 | Young .................. F04B 43/046 250/289 |
| 5,494,036 A | 2/1996 | Uber et al. |
| 5,522,799 A | 6/1996 | Furukawa |
| 5,553,619 A | 9/1996 | Prince |
| 5,563,464 A | 10/1996 | Okubo et al. |
| 5,609,575 A | 3/1997 | Larson et al. |
| 5,631,517 A | 5/1997 | Kato et al. |
| 5,644,199 A | 7/1997 | Nojima et al. |
| 5,713,856 A | 2/1998 | Eggers et al. |
| 5,770,181 A | 6/1998 | Kirkland |
| 5,772,635 A | 6/1998 | Dastur et al. |
| 5,864,331 A | 1/1999 | Anand et al. |
| 5,865,797 A | 2/1999 | Zeeman |
| 5,915,932 A | 6/1999 | Nabity et al. |
| 5,967,484 A | 10/1999 | Morris |
| 5,975,081 A | 11/1999 | Hood et al. |
| 5,984,862 A | 11/1999 | Honda |
| 6,052,614 A | 4/2000 | Morris et al. |
| 6,078,273 A | 6/2000 | Hutchins |
| 6,102,678 A | 8/2000 | Peclat |
| 6,117,115 A | 9/2000 | Hill et al. |
| 6,193,480 B1 | 2/2001 | Butterfield |
| 6,198,285 B1 | 3/2001 | Kormos et al. |
| 6,213,723 B1 | 4/2001 | Danby et al. |
| 6,221,045 B1 | 4/2001 | Duchon et al. |
| 6,230,041 B1 | 5/2001 | Prince |
| 6,240,311 B1 | 5/2001 | Prince |
| 6,243,600 B1 | 6/2001 | Prince |
| 6,248,093 B1 | 6/2001 | Moberg |
| 6,261,262 B1 | 7/2001 | Briggs et al. |
| 6,213,738 B1 | 10/2001 | Danby et al. |
| 6,213,739 B1 | 10/2001 | Phallen et al. |
| 6,316,862 B1 | 11/2001 | Nakata et al. |
| 6,371,732 B1 | 4/2002 | Moubayed |
| 6,406,426 B1 | 6/2002 | Reuss |
| 6,418,337 B1 | 7/2002 | Torchia et al. |
| 6,463,318 B2 | 10/2002 | Prince |
| 6,503,221 B1 | 1/2003 | Briggs et al. |
| 6,516,749 B1 | 2/2003 | Salasidis |
| 6,604,915 B1 * | 8/2003 | Lindler .................. F04B 17/003 417/322 |
| 6,619,051 B1 | 9/2003 | Kilawee et al. |
| 6,629,955 B2 | 10/2003 | Morris |
| 6,635,033 B1 | 10/2003 | Hill et al. |
| 6,641,562 B1 | 11/2003 | Peterson |
| 6,643,537 B1 | 11/2003 | Zatezalo et al. |
| 6,659,978 B1 | 12/2003 | Kasuga et al. |
| 6,685,668 B1 | 2/2004 | Cho et al. |
| 6,749,591 B1 | 6/2004 | McNally et al. |
| 6,848,444 B2 | 2/2005 | Smith et al. |
| 6,881,043 B2 | 4/2005 | Barak |
| 6,889,072 B2 | 5/2005 | Prince |
| 6,893,414 B2 | 5/2005 | Goble et al. |
| 7,044,960 B2 | 5/2006 | Vorhees |
| 7,103,419 B2 | 9/2006 | Engleson et al. |
| 7,124,996 B2 | 10/2006 | Clarke et al. |
| 7,226,430 B2 | 6/2007 | Ludin |
| 7,267,661 B2 | 9/2007 | Susi |
| 7,315,109 B1 | 1/2008 | Griffiths et al. |
| 7,384,410 B2 | 6/2008 | Eggers et al. |
| 7,404,809 B2 | 7/2008 | Susi |
| 7,414,404 B2 | 8/2008 | Keene |
| 7,489,128 B2 | 2/2009 | Kopp |
| 7,545,140 B2 | 6/2009 | Humphreys et al. |
| 7,553,135 B2 | 6/2009 | Cho et al. |
| 7,553,295 B2 | 6/2009 | Susi |
| 7,611,498 B2 | 11/2009 | Hasler |
| 7,753,882 B2 | 7/2010 | Susi |
| 8,105,282 B2 | 1/2012 | Susi et al. |
| 8,148,989 B2 | 4/2012 | Kopp |
| 8,150,493 B2 | 4/2012 | Susi |
| 8,262,642 B2 | 9/2012 | Susi |
| 8,308,452 B2 | 11/2012 | Amirouche et al. |
| 8,378,836 B2 | 2/2013 | Kopp et al. |
| 8,469,932 B2 | 6/2013 | Susi |
| 8,500,694 B2 | 8/2013 | Susi |
| 8,690,829 B2 | 4/2014 | Susi |
| 9,072,577 B1 | 7/2015 | Ferko, III |
| 9,198,584 B2 | 12/2015 | Yamashita et al. |
| 9,585,574 B2 | 3/2017 | Nelson |
| 9,861,743 B2 | 1/2018 | Susi |
| 9,878,089 B2 | 1/2018 | Susi |
| 10,617,821 B2 | 4/2020 | Susi |
| 10,821,223 B2 | 11/2020 | Susi |
| 11,045,600 B2 | 6/2021 | Susi |
| 2001/0014286 A1 | 8/2001 | Peters |
| 2002/0017299 A1 | 2/2002 | Hickle |
| 2002/0025255 A1 | 2/2002 | Wright et al. |
| 2002/0038392 A1 | 3/2002 | De La Huerga |
| 2002/0115933 A1 | 8/2002 | Duchon et al. |
| 2002/0143294 A1 | 10/2002 | Duchon et al. |
| 2002/0165503 A1 | 11/2002 | Morris et al. |
| 2002/0181866 A1 | 12/2002 | Crook et al. |
| 2003/0014035 A1 | 1/2003 | Trombley et al. |
| 2003/0050555 A1 | 3/2003 | Critchlow et al. |
| 2003/0053915 A1 | 3/2003 | Keilman |
| 2003/0058502 A1 | 3/2003 | Griffiths et al. |
| 2003/0171670 A1 | 9/2003 | Gumb et al. |
| 2004/0024434 A1 | 2/2004 | Yang et al. |
| 2004/0030233 A1 | 2/2004 | Frazier et al. |
| 2004/0122486 A1 | 6/2004 | Stahmann et al. |
| 2004/0167465 A1 | 8/2004 | Mihai et al. |
| 2004/0176984 A1 | 9/2004 | White et al. |
| 2004/0179217 A1 | 9/2004 | Chapman |
| 2004/0225341 A1 | 11/2004 | Schock |
| 2004/0249344 A1 | 12/2004 | Nemoto |
| 2004/0256952 A1 | 12/2004 | Puskas |
| 2005/0017910 A1 | 1/2005 | Park |
| 2005/0074340 A1 * | 4/2005 | Xu ........................ F04B 19/006 417/395 |
| 2005/0139002 A1 | 6/2005 | Onishi |
| 2005/0231069 A1 | 10/2005 | Yamazaki et al. |
| 2005/0261563 A1 | 11/2005 | Zhou et al. |
| 2006/0042633 A1 | 3/2006 | Bishop et al. |
| 2006/0085043 A1 | 4/2006 | Stevenson |
| 2006/0160491 A1 | 7/2006 | Eberhart |
| 2006/0173406 A1 | 8/2006 | Hayes et al. |
| 2006/0224141 A1 | 10/2006 | Rush et al. |
| 2006/0229551 A1 | 10/2006 | Martinez et al. |
| 2006/0231238 A1 | 10/2006 | Ball |
| 2007/0049983 A1 | 3/2007 | Freeberg |
| 2007/0064771 A1 | 3/2007 | Schilling |
| 2007/0135797 A1 | 6/2007 | Hood et al. |
| 2007/0179434 A1 | 8/2007 | Weinert et al. |
| 2008/0312512 A1 | 12/2008 | Brukalo |
| 2008/0312584 A1 | 12/2008 | Montgomery |
| 2008/0312585 A1 | 12/2008 | Brukalo |
| 2008/0319393 A1 | 12/2008 | Elder |
| 2009/0270904 A1 | 10/2009 | Birk et al. |

(56) References Cited

U.S. PATENT DOCUMENTS

| | | | |
|---|---|---|---|
| 2010/0059127 A1* | 3/2010 | Shibata | F04B 43/046 137/565.11 |
| 2010/0290935 A1* | 11/2010 | Richter | F04B 43/043 417/413.2 |
| 2010/0331667 A1 | 12/2010 | Nelson | |
| 2011/0061526 A1* | 3/2011 | Wackerle | F04B 43/046 92/96 |
| 2011/0301450 A1 | 12/2011 | Hue et al. | |
| 2014/0377091 A1* | 12/2014 | Delevoye | A61M 5/14212 417/322 |
| 2015/0023821 A1 | 1/2015 | Campbell et al. | |
| 2015/0091573 A1 | 4/2015 | Skloss et al. | |
| 2015/0374537 A1 | 12/2015 | Susi | |
| 2016/0038699 A1* | 2/2016 | Higashiyama | A61M 16/0434 128/207.15 |
| 2016/0131788 A1 | 5/2016 | Kopp | |
| 2017/0113014 A1* | 4/2017 | Nitta | A61M 16/0066 |
| 2018/0209412 A1* | 7/2018 | Wei | F04B 43/04 |
| 2018/0340529 A1* | 11/2018 | Bennett, Jr. | F04B 43/046 |
| 2019/0168213 A1* | 6/2019 | Pulitzer | F04B 23/04 |

FOREIGN PATENT DOCUMENTS

| | | |
|---|---|---|
| EP | 0 602 635 A1 | 6/1994 |
| EP | 0 606 099 A2 | 7/1994 |
| EP | 1 226 839 A1 | 7/2003 |
| JP | 05-084296 | 4/1993 |
| JP | 07-059851 | 3/1995 |
| JP | 07-059853 | 3/1995 |
| JP | 7-178169 | 7/1995 |
| JP | 08-033367 | 2/1996 |
| JP | 08-126627 | 5/1996 |
| JP | 11-148462 | 6/1999 |
| JP | 2001-104478 | 4/2001 |
| JP | 2007 092677 | 4/2007 |
| JP | 05-346054 | 11/2013 |
| WO | WO 95/22999 | 8/1995 |
| WO | WO 02/00276 A1 | 1/2002 |
| WO | WO 2005/026544 | 3/2005 |
| WO | WO 2009/087714 | 7/2009 |
| WO | WO 2009/107008 | 9/2009 |

OTHER PUBLICATIONS

Wang, Jiantao et al. "A Resonant Piezoelectric Diaphragm Pump Transferring Gas with Compact Structure", Jilin University, Dec. 1, 2016.

Ham, Young Bog et al., "Development of a Piezoelectric Pump for a Highly-precise Constant Flow Rate" Korea Institute of Machinery and Materials, Jul. 14, 2010.

* cited by examiner

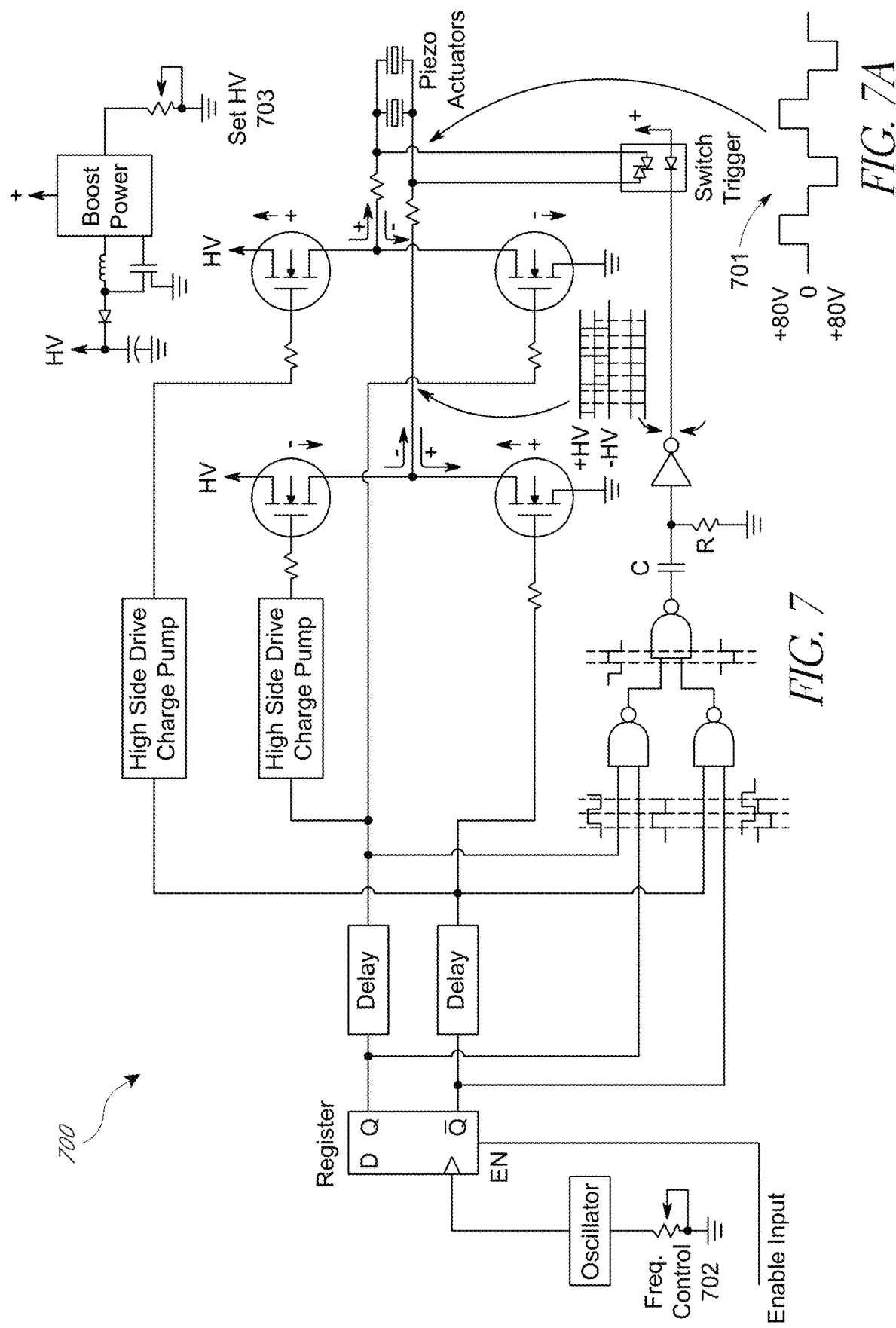

FLUID PUMPS FOR USE IN MRI ENVIRONMENT

FIELD

This disclosure relates to apparatuses for pumping fluid (e.g., gas or liquid) in a magnetic resonance image (MRI) environment of high magnetic fields and required low radiofrequency interference.

BACKGROUND

Non-invasive blood pressure (NIBP) and respiratory gas monitors are used throughout hospitals and other medical facilities to monitor the health of patients. Typically, non-invasive blood pressure monitors pump air to a blood pressure cuff and determine the pressure at which blood is flowing through the patient's arteries. Patient metabolic processes produce carbon dioxide ($CO_2$) and anesthetic procedures make use of various gases to produce anesthetic effects. It is desirable to monitor such gases and the blood pressure, as well as other characteristics of a patient, including while the patient is in an MRI environment. However, the pumps and electronics in many blood pressure and gas analyzer monitors include components, such as motors or pumps which cannot be used safely in an MRI environment, primarily due to the ferrous materials used or magnetic fields produced by the common motors and pumps used for blood pressure and gas analyzer monitors. Ferrous materials present a risk of becoming a projectile and striking patients or attending clinical staff.

SUMMARY

In accordance with several embodiments, a non-magnetic pump configured for safe and effective use within an MRI environment includes a pump housing forming a pump chamber within the housing, a piezoelectric member (e.g., plate, disc) positioned inside the pump housing, an exhaust port operably connected to the pump chamber, a valve positioned between the pump chamber and the exhaust port, an inlet port operably connected to the pump chamber, a valve positioned between the pump chamber and the inlet port and a drive circuit configured to energize the piezoelectric member. The piezoelectric member, when energized, is configured to deflect into the pump chamber, leaving a dead space of less than 35% (e.g., less than 35%, less than 30%, less than 25%, less than 20%, less than 15%, less than 10%, less than 5%) of the pump chamber's volume when the piezoelectric member is un-energized.

In some embodiments, the pump housing includes an upper housing and a lower housing, wherein the upper housing and the lower housing are attached to form the pump housing. A piezoelectric assembly or member (e.g., piezoelectric plate, disc) is positioned between the upper housing and the lower housing. The piezoelectric assembly or member may include two or more discs or plates (e.g., a first piezoelectric disc, a second piezoelectric disc, and a silicon disc or elastomeric carrier comprising a first side and a second side. The first piezoelectric disc may be positioned on the first side of the silicon disc or within a first recess of one side of an elastomeric carrier and the second piezoelectric disc may be positioned on the second side of the silicon disc or within a second recess of the opposite side of the elastomeric carrier. The piezoelectric assembly positioned between the upper housing and the lower housing may form an upper chamber and a lower chamber. For example, the space between a top surface of the first piezoelectric disc and a bottom surface of the upper housing (or valves located within the upper housing) may constitute the upper chamber and the space between a bottom surface of the second piezoelectric disc and a top surface of the lower housing (or valves located within the lower housing) may constitute the lower chamber. The silicon disc or an insulation member or layer of the elastomeric carrier may advantageously electrically insulate the first piezoelectric disc from the second piezoelectric disc.

The first piezoelectric disc and the second piezoelectric disc may operably be connected to the drive circuit such that the piezoelectric discs deflect in one direction (e.g., toward the upper housing) when positive voltage is applied by the drive circuit and such that the piezoelectric discs deflect in an opposite direct (e.g., toward the bottom housing) when negative voltage is applied to the drive circuit. In some embodiments, the upper chamber is formed in a shape substantially similar to the shape of the piezoelectric disc when positive voltage is applied by the drive circuit and the lower chamber is formed in a shape substantially similar to the shape of the piezoelectric disc when negative voltage is applied by the drive circuit.

The drive circuit may be configured to energize the piezoelectric plate with a sinusoidal or pseudo-sinusoidal wave. The wave may have a voltage in the range of 20 to 180 volts peak to peak (e.g., 20 to 80 volts peak to peak, 40 to 120 volts peak to peak, 80 to 180 volts peak to peak, 120 to 180 volts peak to peak, 60 to 100 volts peak to peak, overlapping ranges thereof, or any value within the recited ranges). The wave may have a frequency between 20 Hz and 240 Hz (e.g., between 20 Hz and 100 Hz, between 60 Hz and 140 Hz, between 80 Hz and 200 Hz, between 120 Hz and 240 Hz, overlapping ranges thereof, or any value within the recited ranges).

In accordance with several embodiments, a non-invasive blood pressure monitor configured for safe and effective operation within an MRI scan room without interfering with operation of an MRI scanner or images acquired by the MRI scanner is provided. The monitor unit includes a blood pressure cuff (e.g., arm cuff), an air bladder disposed within the cuff, and a non-magnetic pump operably connected to the air bladder to provide pressurized air to the air bladder.

In one embodiment, the non-magnetic pump is a piezoelectric pump including a pump housing forming a pump chamber within the housing, a piezoelectric plate located inside the pump housing, an exhaust port operably connected to the pump housing, a valve positioned between the pump chamber and the exhaust port, and a drive circuit configured to energize the piezoelectric plate, wherein the piezoelectric plate, when energized, deflects into the pump chamber.

In a second embodiment, the non-magnetic pump is a rotary ultrasonic motor driven pump that includes a rotary ultrasonic motor formed of a rotor/stator assembly, a diaphragm air pump comprising a first pump chamber and a first diaphragm, and a drive circuit. The ultrasonic motor may operably be connected to the diaphragm air pump with a piston or drive shaft. The drive circuit may be configured to cause the ultrasonic motor to move the piston, and thereby move the first diaphragm of the diaphragm air pump. In some embodiments, the diaphragm air pump includes a second pump chamber and a second diaphragm. The pump may include an eccentric cam configured to control inflation and deflation of the two diaphragms in alternating fashion, thereby doubling the output speed and air of the pump. The rotor of the ultrasonic motor may include a spring. The ultrasonic motor may be driven by a multiphasic electronic signal with little (e.g., an amount insufficient to cause any appreciable effect) RF harmonic noise in the spectral range of about 6 or 8 MHz to about 130 MHz in which MRI receivers are most sensitive. In some embodiments, the drive power for the ultrasonic motor is generated via circuitry which produces multiphasic drive signals of at least sine and cosine waveforms at related ultrasonic frequencies of approximately 40-46 kHz and 90 V to 110 Vrms or approximately 300 V peak-peak (Vpp). These drive signals may advantageously be produced as a sinusoidal wave to reduce high frequency harmonic components which may disturb RF responsiveness. The diaphragm air pump may also include one or more heat sinks thermally coupled to the ultrasonic motor and adapted to remove or dissipate heat (e.g., by thermal conduction) generated by the ultrasonic motor (e.g., from the friction between the rotor and the stator). The diaphragm air pump may also include a force-amplified piezoelectric valve that is configured to facilitate controlled leakage of air out of the blood pressure cuff (e.g., bladder of the arm cuff).

BRIEF DESCRIPTION OF THE DRAWINGS

FIGS. 3C-1 to 3C-3 are cross-section views of the assembled piezoelectric pump of FIG. 3B at various stages of operation.

FIG. 7 is a schematic circuit diagram of drive electronics, or drive circuitry, for the piezoelectric pump of FIGS. 4A to 4C-3. FIG. 7A illustrates an example pseudo-sine wave output voltage signal of the drive electronics circuit of FIG. 7.

DETAILED DESCRIPTION

Figure 1:
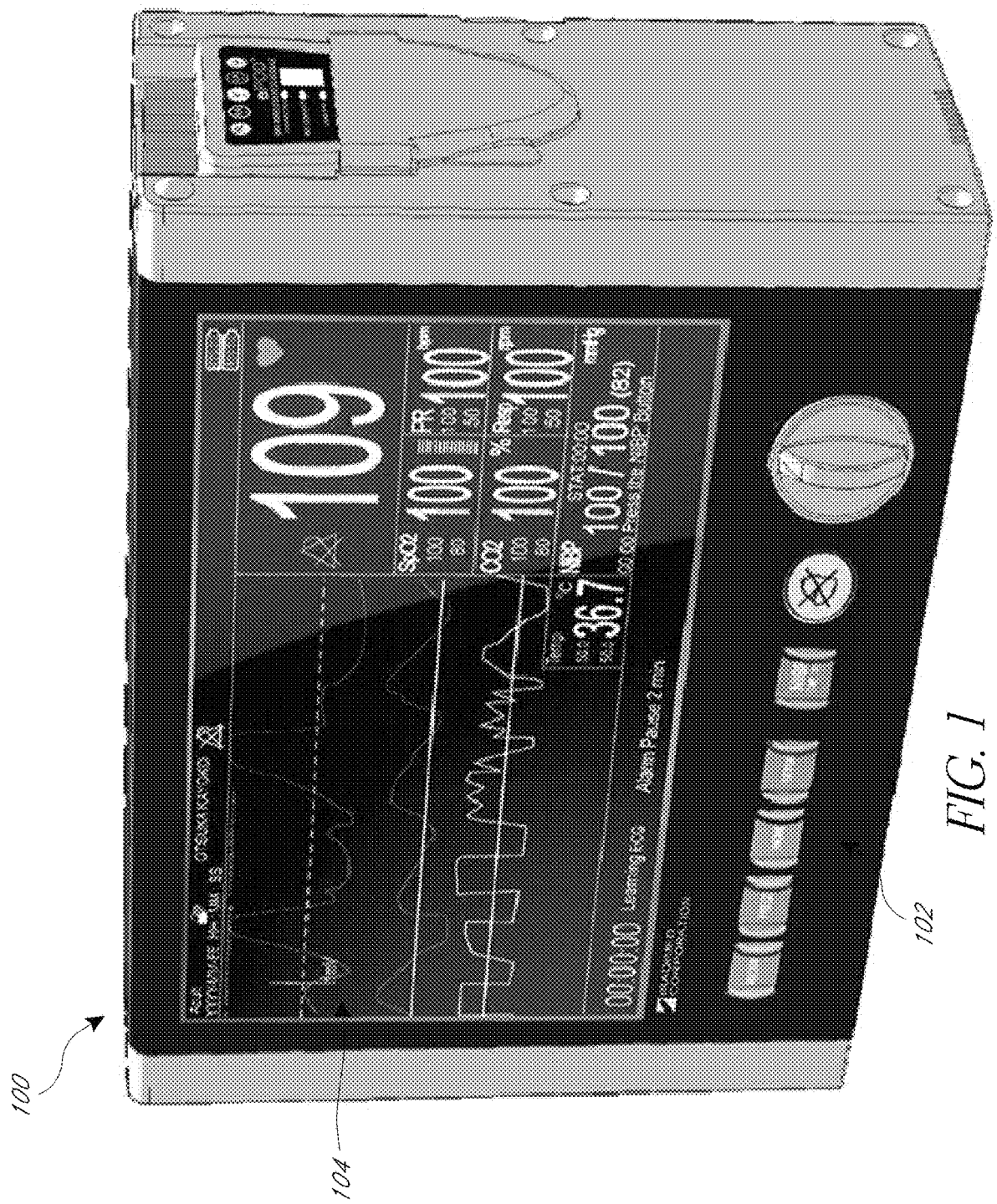
FIG. 1 illustrates an embodiment of a multi-parameter patient monitor configured for safe and effective use in an MRI environment.

The high magnetic field surrounding MRI systems can negatively affect the operation of various devices, especially those devices that are constructed with magnetic (e.g., ferrous) materials, and can seriously jeopardize a patient's safety as a result of devices utilizing magnetic materials that can be attracted at high velocity into the magnetic field where a patient or attendant personnel are located.

Medical devices intended to be used within the MRI environment may require special consideration. Radiofrequency (RF) stimulation of atomic nuclei within an associated magnetic field results in the emission of a small RF spin echo from the nucleus so stimulated. In the case of patient imaging, hydrogen nuclei bound with water are the usual targets for magnetic resonance at selected frequencies. Other molecules and compounds can also be selected for study, as in Nuclear Magnetic Spectroscopy, by choosing resonance specific magnetic field strengths and associated radio frequencies. For simplicity, the typical hydrogen atom-based image-acquisition process is referred to herein, but it should be recognized that the disclosure is equally useful in spectrographic studies at a plurality of field strengths and frequencies.

Certain devices may be needed to be close to the patient within the highly magnetic center bore of an MRI scanner in the MRI scan room either to assist with care of the patient being imaged or for the use of attending staff. Of particular interest are those devices placed in the scan room during the time of image acquisition when the patient is present and the magnetic fields are up and RF reception of the tiny nuclear echoes must be cleanly acquired. Electrically passive but magnetic metallic items such as oxygen bottles or crash carts present safety hazards to the patient or attending staff due to their potential to be strongly attracted by the magnetic field of the scanner. Such items can be pulled into the high magnetic field region of the imaging volume where the patient is located, creating potential for serious injury or death. Additionally, great effort is made during the manufacture and installation of the scanner/magnet to assure that the lines of flux within the imaging volume are highly homogenous to assure that acquired images have minimal spatial distortion. Thus, devices formed of magnetic material that are positioned within the magnetic field of the scanner can introduce distortions into this homogeneous field and the resultant images. The level of hazard and the degree of field/image distortion due to magnetic materials depends upon the composition and location with respect to the imaging volume.

The hazards due to flying objects can be controlled to some degree by the use of non-ferrous devices, such as an aluminum oxygen bottle, instead of a steel oxygen bottle. Additionally, the gravitational weight of some devices or their rigid fixation in the scanning room may be sufficient to overcome the force of magnetic attraction on the ferrous mass of such devices toward the imaging volume. However, such devices with some ferrous mass, though inhibited from being pulled into the magnetic field, may nevertheless introduce inhomogeneity in the magnetic field. In accordance with several embodiments, distortions in the homogeneity of the magnetic field within the imaging volume is kept at such a level as to be of minimal consequence to the operator reading the resultant image or data. And, the possibility of field distortion is proportionally increased as devices with metallic materials are positioned closer to the imaging volume, with the most critical position being near the center of the imaging volume, essentially where the patient is positioned.

Additionally, because of the extremely low levels of RF signals produced by the target image nuclei, great care may be taken to assure that devices with active electronic circuits do not emit spurious RF signals as forms of electronic noise.

Such noise can so degrade the signal-to-noise ratio of signals received by the sensor coils and receivers that image resolution is reduced or rendered completely unreadable. Active circuits may be carefully shielded to assure that their RF emissions are extremely low at the specific frequencies of the imaging process. Conversely, it is possible through careful design, to place electrical circuits for the operation of medical devices, or the like, within the MRI environment, but such circuits may be designed to avoid the discreet Larmor frequencies unique to the particular magnetic field strength of a given scanner. The intense magnetic fields produced by the scanner can cause detrimental effects on the performance of common DC and stepper motors in devices needed within the scanning room, to the point of making their control difficult or causing their complete failure. The gradient or time-varying magnetic fields can induce changing (AC) currents in motors and associated circuitry which may also cause false motor operation.

Monitoring System

FIG. 1 shows an embodiment of a multi-parameter monitor 100 (e.g., patient monitor) configured for safe and effective use in the MRI environment. The monitor 100 may advantageously be operated safely in a 30,000 Gauss magnetic field (e.g., within or near an MRI bore or imaging volume) without the need for fixed mounting or a heavy cart and provides continuity of care from a care unit to an MRI suite and back to the care unit. The multi-parameter monitor 100 may be configured to monitor and display waveform graphs and/or real-time values of multiple physiological parameters, for example but not limited to, temperature, blood oxygen saturation levels (SpO2), ECG, heart rate, pulse rate, carbon dioxide ($CO_2$), anesthetic gases, respiratory rate, and/or blood pressure. The monitor 100 may include one or more lights configured to be activated using different colors depending on severity of an alert. For example, the monitor 100 may have a multicolor, severity-based dome light (not shown) positioned on top of the monitor 100 that is visible from all sides of the monitor. Temperature may be monitored using one or more fiber optic patient temperature devices. As shown, the monitor 100 may include multiple physical buttons or switches 102 for frequently used activities, such as a settings or set up button, a freeze or pause button, a record button, a print button, a trend display button, an alarm silence button, MEP start/stop button, and/or the like. The monitor 100 includes a display screen 104 adapted to display waveform graphs and/or real-time values of various parameters associated with the patient or the environment of the patient. The monitor 100 may also be configured to display dynamic messages that are color coded based on severity or priority.

Figure 2:
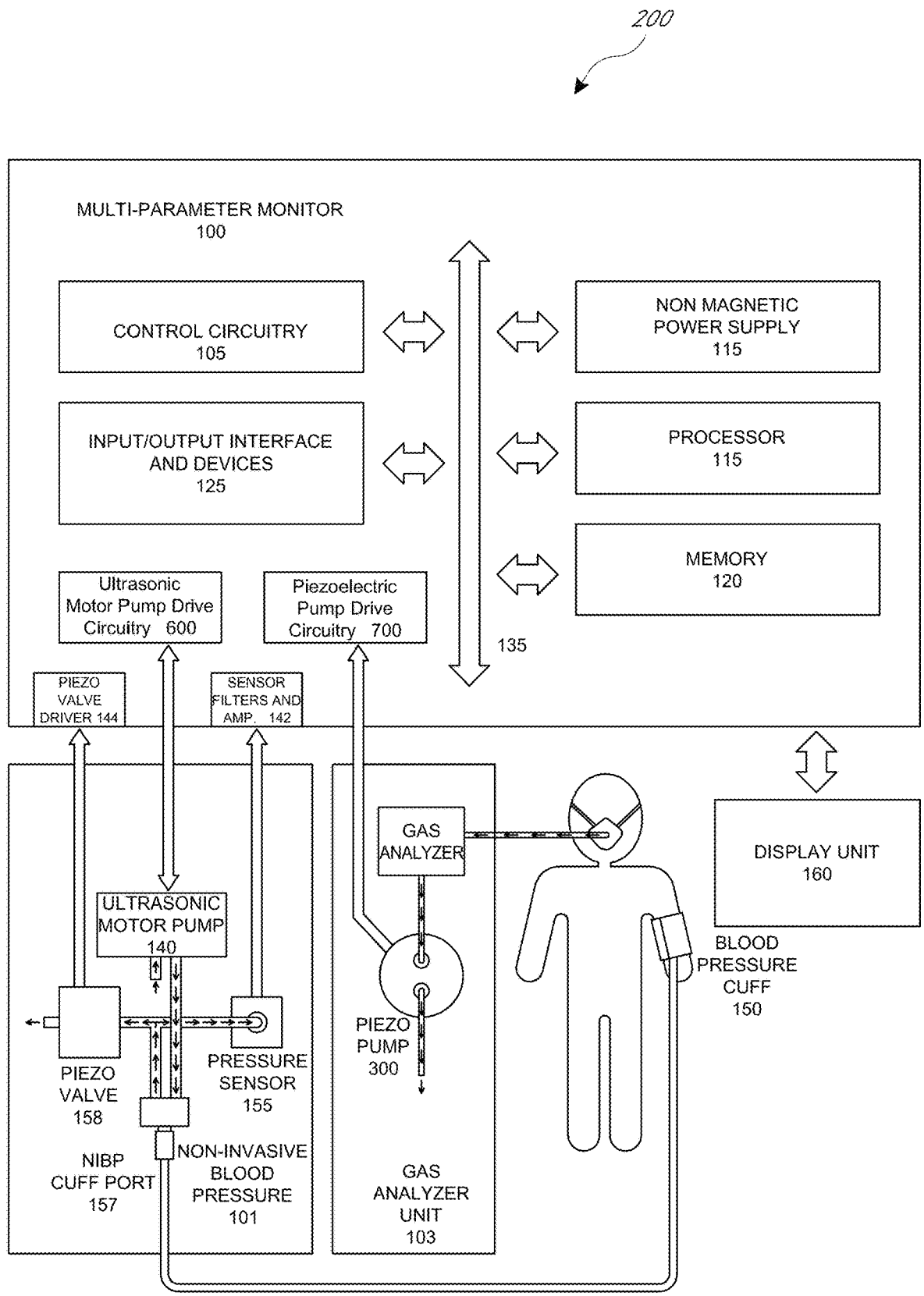
FIG. 2 is a schematic drawing of an embodiment of a multi-parameter patient monitoring system configured for safe and effective use in an MRI environment.

FIG. 2 shows a schematic block diagram of an embodiment of a multi-parameter monitoring system 200 that includes the multi-parameter patient monitor 100 and one or more sub-module units configured to interface and communicate with the multi-parameter patient monitor 100. In some embodiments, the multi-parameter monitor 100 may include an integrated, or built-in, display 160 or may be connected to a separate display unit. In the illustrated schematic embodiment, the multi-parameter monitor 100 includes a non-invasive blood pressure monitoring unit 101 and a gas analyzer unit 103. The multi-parameter monitor 100 also includes control circuitry 105, a non-magnetic power supply 110, a processor 115, memory 120, and input/output interfaces and devices 125. The various components or modules of the multi-parameter monitor 100 and the components or modules that the multi-parameter monitor 100 interfaces with may communicate with each other via a bus or other communication line 135 or via wireless communication protocols and techniques.

The non-invasive blood pressure monitoring unit 101 may further include a non-magnetic pump 140 actuated by an ultrasonic motor (e.g., rotary ultrasonic motor), a blood pressure cuff 150, one or more pressure sensors 155, a cuff port 157 and a force-amplified piezoelectric valve 158. The blood pressure cuff 150 may be attached to the blood pressure monitoring unit 101 (and its non-magnetic ultrasonic motor (USM) driven pump 140) through one or more tubes that direct air flow to the blood pressure cuff 150. The control circuitry 105 may include circuitry and electrical components designed to drive the non-magnetic USM driven pump 140, analyze input to determine blood pressure readings, and control the pressure in the blood pressure cuff 150 (such as a piezo valve driver 144, ultrasonic motor pump drive circuitry 600 (e.g., including a 40 kHz, 300 Vpk-pk sin/cos driver) and one or more sensor filters and amplifiers 142). The control circuitry 105 (in combination with the processor 115) may output blood pressure readings for display on the display unit 160. The force-amplified piezoelectric valve 158 is configured to facilitate control of leakage of air out of the blood pressure cuff 150. In some embodiments, the non-invasive blood pressure unit 101 may include additional control circuitry. In some embodiments, the non-invasive blood pressure unit 101 operates independently of a multi-parameter monitor or operates with a dedicated blood pressure monitor or a display module. Although illustrated as separate boxes in FIG. 2, the drive circuitry, drivers, filters and/or amplifiers may be components within control circuitry 105 or input/output interface and devices module 125 or may be physically located on the blood pressure monitoring unit 101 itself. In addition, the force-amplified piezo valve 158 and the pressure sensor 155 could be physically located on the multi-parameter monitor board with control circuitry 105 instead of on a board with the non-invasive blood pressure monitoring unit 101.

The processor 115 may be any hardware computing device, such as a central processing unit or microcontroller. The controller 115 may be implemented using a single computing device or multiple computing devices. In some embodiments, the processor 115 may analyze signals to determine blood pressure readings, interpret inputs from input/output interfaces and devices 125, operate the control circuitry 105, and communicate with other systems, such as the display unit 160, for example.

The housing of the multi-parameter monitor 100, the blood pressure monitoring unit 101, gas analyzer unit 103, or portions thereof, may include shielding or filtering materials or devices to prevent spurious emissions of radiofrequency energy that could potentially distort or degrade images obtained by MRI equipment. The components of the multi-parameter monitor 100, the blood pressure monitoring unit 101 and gas analyzer unit 103 may be on a single circuit board, on three separate circuit board assemblies or on two circuit board assemblies. The three units may be separate stand-alone units or integrated as a single unit. The physical location of the various components can be re-arranged without departing from the scope of the disclosure.

The processor 115 may also communicate with memory 120. The memory 120 may contain computer program instructions (organized into modules) that the processor 115 executes in order to implement one or more embodiments of the present disclosure. The memory 120 may include RAM, ROM, other persistent or non-transitory computer-readable media, or some combination of memory elements. The memory 120 may store an operating system that provides computer program instructions for use by the processor 115 in the general administration and operation of the processor 115. The memory 120 may further include other information for implementing aspects of the present disclosure.

The input/output interfaces and devices 125 may include one or more input ports, including, but not limited to, user-actuated controls, paddle and network connector ports, Bluetooth or other wireless links, optical ports, USB ports, cuff ports, gas sampling ports, and/or the like. The input/output interfaces and devices 125 may accept input from or one or more input devices, including, but not limited to, keyboards, mice, trackballs, trackpads, joysticks, input tablets, track points, touch screens, remote controls, game controllers, heart rate monitors, velocity sensors, voltage or current sensors, motion detectors, cameras, microphones, or any other input device capable of obtaining a position or magnitude value from a user. In some embodiments, the input devices may include devices or connectors configured to receive power from a power supply of a multi-parameter monitor and provide power to the blood pressure monitoring unit 101 and/or gas analyzer unit 103 when the units are connected to the multi-parameter monitor 100.

The input/output device interfaces and devices 125 may also provide output via one or more output devices, including, but not limited to, one or more speakers or any of a variety of digital or analog audio capable output ports, including, but not limited to, headphone jacks, XLR jacks, stereo jacks, Bluetooth links, RCA jacks, optical ports or USB ports. In some embodiments, the input/output device interfaces and devices 125 include an I/O port and/or connector configured to facilitate communication between the blood pressure monitoring unit 101 and a multi-parameter monitor 100 and/or a gas analysis unit 103. For example, the input/output device interfaces and devices 125 may include a serial A/D connector. In some embodiments, a blood pressure reading generated by the blood pressure monitoring unit 101 and/or the gas readings of the gas analysis unit 103 may be output to the multi-parameter monitor 100 for output on the display 104 of the multi-parameter monitor 100. The input/output devices 125 may be configured to generate visible light and/or audible alarms. Further display and monitor control may be implemented with a remote control device with display and user controls, or via networked communications. The remote display and control device may be a tablet-like handheld portable device with wireless communications to the monitor 100 or a base communications relay unit.

Examples of Parameters to Be Monitored by Multi-Parameter Monitor

Figure 5A:
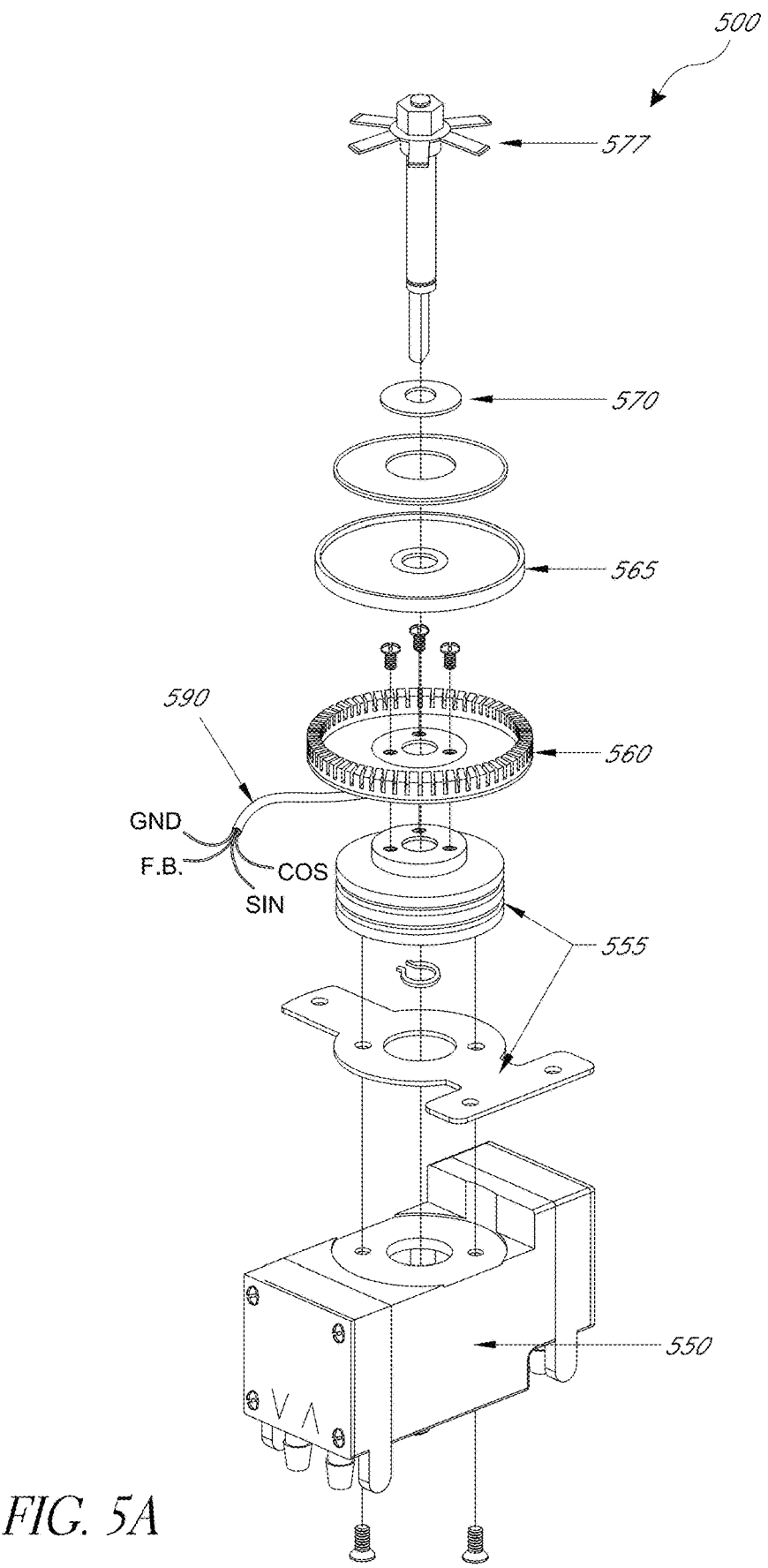
FIG. 5A is an exploded assembly view of an embodiment of a non-magnetic ultrasonic motor driven pump (e.g., rotary ultrasonic motor driven pump) configured for safe and effective use in an MRI environment.
Figure 5B:
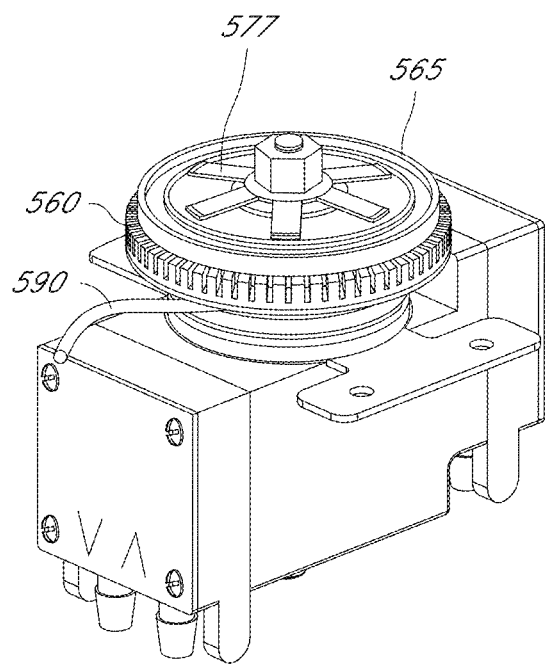
FIG. 5B is a perspective view of the assembled ultrasonic motor driven pump of FIG. 5A.
Figure 5C:
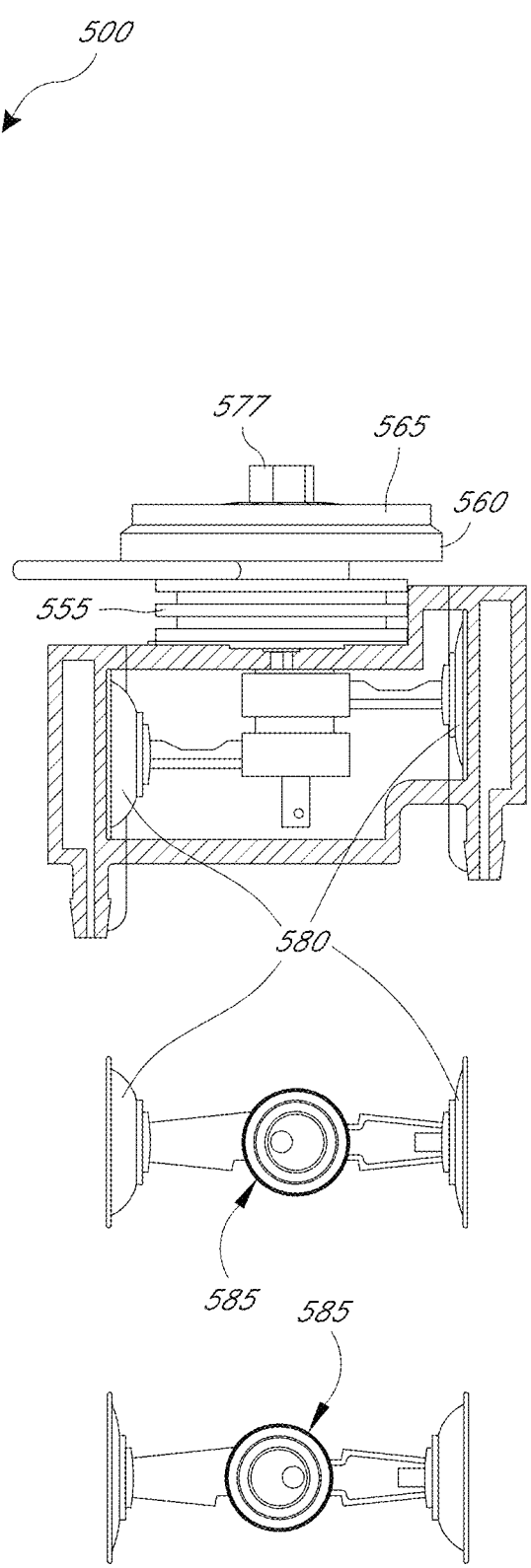
FIG. 5C illustrates a side cross-section view of the assembled ultrasonic motor driven pump of FIG. 5A as well as top views of the cam and pump valves at different stages of operation.

Some of the parameters to be monitored by the multi-parameter monitor 100 may require the use of fluid pumps (e.g., air pumps, suction pumps). For example, the gas analyzer unit 103 may incorporate the use of a non-magnetic piezoelectric diaphragm pump and the NIBP monitoring unit 102 may incorporate the use of a non-magnetic USM driven pump (e.g., rotary USM driven pump as shown in FIGS. 5A-5C). Gases (e.g., carbon dioxide, nitrous oxide, or anesthetic gases) from the subject's breath are often analyzed with infrared absorption techniques with a gas analyzer physically located within the multi-parameter monitor 100 or elsewhere remote from the subject. In such situations, known as "sidestream" analyzers, the gas sample must be drawn via suction from the patient's airway to the analyzer through a small tube. This typically requires a suction flow rate of between 25 and 300 mL/hour at −50 to −400 mBar. Current devices perform this gas sampling with small electrically-motorized pumps using common DC motors, which present a potential for magnetic attraction in the MRI environment and also may stall in the presence of high external magnetic fields near the MRI machine.

A NIBP monitoring device (e.g., non-invasive blood pressure monitoring unit 101) enables measurement of a patient's blood pressure. Typically, this is done by inflating an air bladder inside a blood pressure cuff around the patient's arm. In some embodiments, blood pressure cuffs may be applied to other positions on a patient's body, such as the patient's wrist or finger or leg. NIBP monitors may measure the systolic blood pressure, diastolic blood pressure, mean blood pressure, and/or other blood pressure elements. Systolic blood pressure is the maximum blood pressure in a patient's artery during a pumping cycle of the patient's heart. For healthy patients, this occurs immediately after the patient's heart pumps blood from the left atrium. Diastolic blood pressure measures the minimum blood pressure in a patient's arteries during one pumping cycle. In a healthy heart, this occurs just before the heart pumps blood from the left atrium at the beginning of another cycle.

To measure a patient's blood pressure, a blood pressure cuff is inflated to apply pressure to one of the patient's major arteries (e.g. the brachial artery). When the blood pressure cuff is pressurized above the patient's systolic blood pressure, the artery collapses and the blood flow is stopped. As air is released from the blood pressure cuff (which conventionally was performed by an electrically-controlled valve that itself is a magnetic device), the pressure applied by the blood pressure cuff will drop. At some point, the pressure in the cuff will drop below the patient's systolic blood pressure and some blood flow will resume through the patient's arteries. As more air is released from the blood pressure cuff, more blood at lower pressures is able to flow through the patient's artery. When the pressure in the cuff drops below the patient's diastolic blood pressure blood is able to flow freely through the patient's artery. A physician or medical device may recognize the sound of the resumed blood flow or may receive other indications of the blood flow. For example, sensors 155 connected to the blood pressure cuff (e.g., cuff 150) may receive indications of oscillations in pressure caused by intermittent blood flow passing through the patient's artery. The signals from the oscillations may be interpreted by the medical device to determine one or more measurements for the patient's blood pressure.

An air pump (e.g., non-magnetic USM driven pump 140) may be used to provide air pressure to the blood pressure cuff. The high magnetic field surrounding MRI systems can negatively affect the operation of various conventional devices (including pumps and related devices), especially those conventional devices that are constructed with magnetic materials, and can seriously jeopardize a patient's safety as a result of the conventional devices utilizing magnetic materials that can be attracted at high velocity into the magnetic field where patient or attendant personnel are located. In addition, some conventional pumps and valves may be rendered inoperable by the magnetic fields surrounding MRI systems. Conventional pumps operating within MRI environments may also be selected and shielded to avoid creating RF interference, which may degrade the signals received by the MRI machine and reduce the image resolution.

Piezoelectric Pumps

Figure 3A:
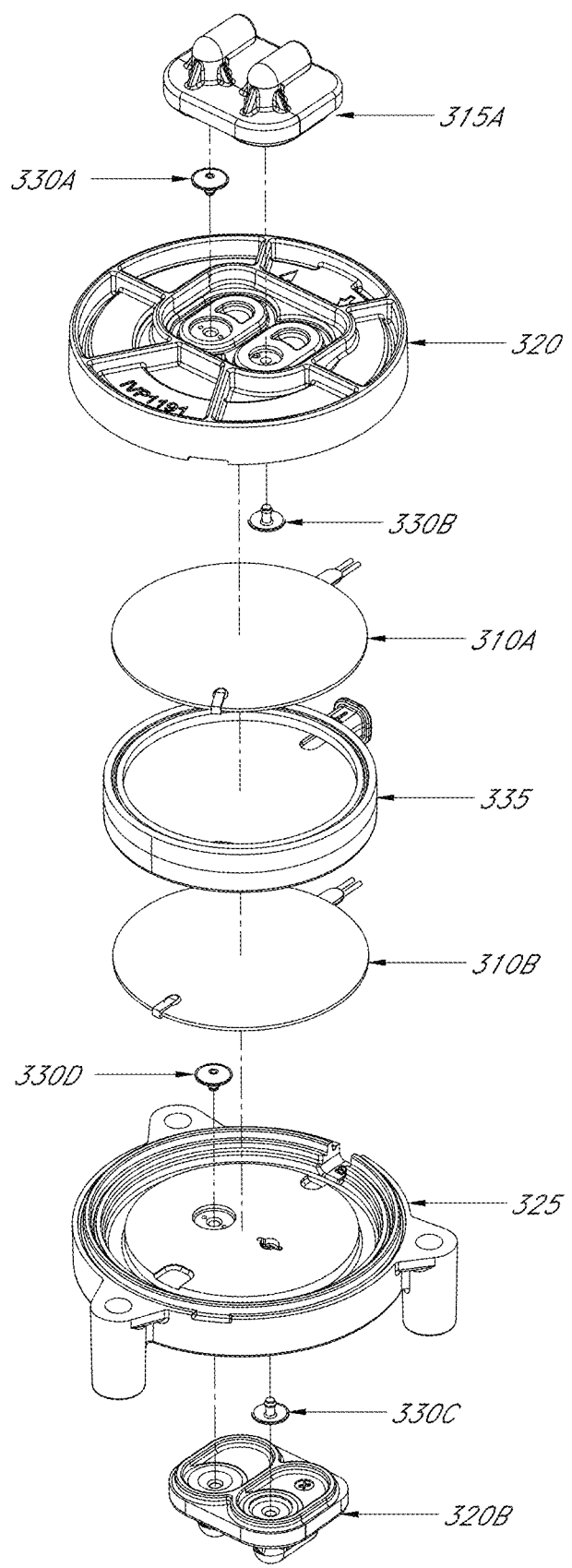
FIG. 3A is an exploded assembly view of an embodiment of a piezoelectric pump configured for safe and effective use in an MRI environment.
Figure 3B:
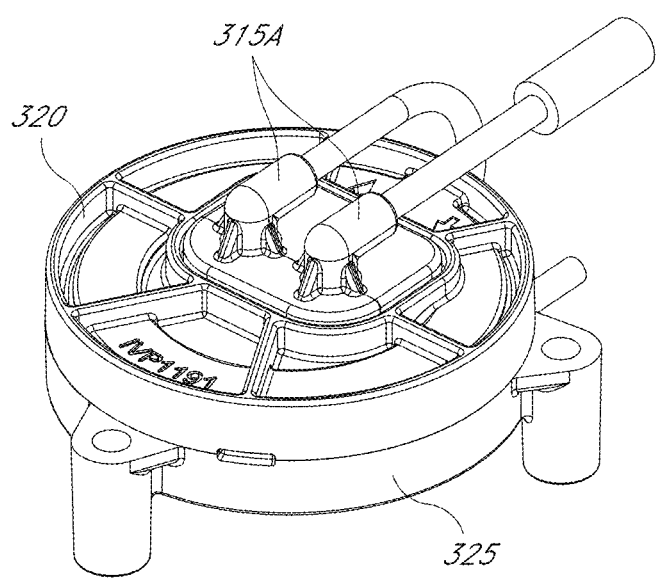
FIG. 3B is a perspective view of the assembled piezoelectric pump of FIG. 3A.

The non-magnetic piezoelectric pump 300 may operate by moving fluid (e.g., air) with a piezoelectric disc or other member that flexes into a domed shape when energized with an electrical charge. FIGS. 3A and 3B illustrate components or parts and assembly of one embodiment of such a piezoelectric pump 300. The components or parts include one or more piezoelectric members 310, fluid ports 315A, 315B, top housing 320, bottom housing 325, valves 330A-330D, and an elastomeric carrier 335. As shown, the piezoelectric members 310 may consist of a top piezoelectric plate or disc 310A and a bottom piezoelectric plate or disc 310B. The piezoelectric members 310 may be comprised of any piezoelectric material capable of deflecting in response to an applied electrical charge. For example, the piezoelectric members 310 may be formed of flat ceramic material. In some embodiments, the piezoelectric members comprise discs having a diameter of approximately 2.5 inches and the thickness of each member may be approximately 0.05 inches. In some embodiments, the piezoelectric members 310 have a diameter in the range of 1-2 inches, 1.5-2.5 inches, 2-3 inches, 0.5-1.5 inches, overlapping ranges thereof, or any value within the recited ranges. The thickness may be in a range of 0.025 to 0.075 inches, 0.04 inches to 0.06 inches, 0.05 inches to 0.10 inches, overlapping ranges thereof, or any value within the recited ranges.

The piezoelectric members 310 may have a circular disc shape as shown or may have other shapes as desired and/or required. Electrical leads 340 are coupled to the piezoelectric members 310 to provide an electrical charge across one or more of the piezoelectric members to energize the piezoelectric member(s) 310 to cause the desired deflection. The leads 340 may be connected to the piezoelectric pump drive circuitry 700 illustrated in FIGS. 2 and 7 or another power or voltage source capable of providing sufficient charge to energize the piezoelectric members 310.

The piezoelectric members 310 provide the mechanical driving force within the pump housing. When a piezoelectric member (e.g., disc) is energized by providing voltage through leads 340, it flexes into a domed shape, rising to a peak deflection height in the center. The dome rises upwards with one polarity and downwards with the opposite polarity. When there is no potential difference between leads 340, the piezoelectric member (e.g., disc) is not energized and it remains in a flat state.

In some embodiments, the elastomeric carrier 335 comprises a one piece disc spacer and gasket part that forms a single molded, non-separable, integral unit. The elastomeric carrier 335 may include recesses (e.g., top and bottom recess) shaped, sized and molded to receive a respective one of the piezoelectric members 310 and may be configured to provide shock, vibe and gasket mount for the piezoelectric members 310. The elastomeric carrier 335 advantageously prevents the piezoelectric members 310 from damaging each other as they flex or deflect, as the two piezoelectric members 310 may not flex in a perfectly-matched pattern. The elastomeric carrier 335 may also electrically insulate the piezoelectric members and/or electrically isolate them from each other. Portions of the piezoelectric members 310 may be permanently adhered or coupled to the elastomeric carrier 335.

The deflection amplitude, force, and other properties of the piezoelectric members 310 can be controlled by choosing different piezoelectric materials as well as by the drive voltage. As discussed above, depending on the desired characteristics, the piezoelectric members 310 may be made out of one or more of a variety of materials with piezoelectric properties. Depending on the piezoelectric material used, the pump 300 may require different driving circuits to energize the piezoelectric members 310, and may have different minimum and maximum operating parameters.

In piezoelectric pump 300, the piezoelectric disc 310 is housed between top housing 320 and bottom housing 325. Each housing element is shaped to create a fluid chamber between the housing and the piezoelectric disc 310 when the disc is in a non-energized state. In some embodiments, the pump chambers are configured to very closely match or conform to the domed shape of the piezoelectric disc 311 when fully energized, thereby minimizing the dead fluid space within the chamber, and in turn maximizing the volume of fluid flow and the pressure provided by the pump 300. In accordance with several embodiments, careful control of the electrical drive voltage and wave shape is needed, especially since the optimal pump chamber leaves only a small dead space or the housing 320, 325 doesn't closely match the shape of the energized piezoelectric disc 310, the disc 310 may contact the chamber wall when driven at its maximum voltage, which may lead to increased pump noise or may break the piezoelectric disc 310 or other pump elements. If the pump chamber is too large or the housing doesn't match the deflected shape of the energized piezoelectric disc 310, there will be more useless dead space in the chamber when the piezoelectric disc 310 is energized, which leads to decreased output volume and a decrease in maximum pressure output from the pump 300, especially when pumping air and/or other gases. It should be noted that the piezoelectric pump 300 can operate both as a pressure and/or suction pump, and can be configured to pump other fluids in addition to air, such as other gases, or even liquids. In the case of non-compressible media such as water, elimination of dead space is not so critical as when pumping compressible fluids such as air.

Top and bottom housings 320, 325 may be advantageously made of a non-magnetic material, such as a polymer (e.g., plastic) and/or non-ferrous metals, such as aluminum or brass. The top and bottom housings 320, 325 may be attached to form a closed chamber that contains the piezoelectric member 310 (e.g., plate, disc). In some embodiments, the housings 320, 325 are attached with non-magnetic screws or using adhesives or snap-fit or friction-fit engagement mechanisms. When a piezoelectric member 310 is energized, it deflects into an empty chamber formed between the energized piezoelectric member 310 and either the top housing 320 or bottom housing 325, depending on which piezoelectric member 310 is energized, and the polarity of the driving energy (e.g., voltage). The deflection of the energized piezoelectric member 310 into the chamber (e.g., chamber 370 in FIGS. 3C-1 to 3C-3) forces fluid (e.g., air) out of the chamber through a respective exhaust valve 330A, 330C and fluid port 315A, 315B, as will be described in more detail below in connection with FIGS. 3C-1 to 3C-3.

The fluid ports 315 may, in some embodiments, be made of the same material as the top and bottom housings 320, 325, or may be made out of another non-magnetic material. The fluid ports 315 may be connected to the top and bottom housings 320, 325 in the same manner as the housings are connected to each other or in another manner. In some embodiments, the connections between the fluid ports 315 and the top and bottom housings 320, 325 may be sealed with one or more O-rings, or made as one single monolithic piece using molding methods.

The valves 330 include both exhaust valves 330A, 330C and intake valves 330B, 330D. The exhaust valve 330A is associated with one of the top fluid ports 315A and the intake valve 330B is associated with the other one of the top fluid ports 315A. The exhaust valve 330C is associated with one of the bottom fluid ports 315B and the intake valve 330D is associated with the other one of the bottom fluid ports 315B. The valves 330 may be positioned between the fluid chambers formed between a respective housing 320, 325 and piezoelectric member 310 and the fluid ports 315 to regulate the flow of fluid in the pump 300. The valves 330 also have a fixed valve cavity "dead space" associated with them. To maximize the fluid volume and pressure provided by the pump 300, it may be advantageous to use valves capable of rapidly opening and closing, in relation to the operating frequency chosen or determined and with such minimal profile so as to consume little to no dead space in the valve cavity. Since the deflections of piezo ceramic materials are small, valves which open relatively slowly or with higher cracking pressure will not respond until the deflection has moved for significant portions of the overall total deflection distance, thereby wasting a portion of the intake cycle Likewise, slow and/or high cracking force valves introduce inefficiency during the exhaust cycle, both by opening late and wasting piezo deflection through compression of the fluid (e.g., air) as well as by allowing a regurgitation of the exhausted fluid (e.g., air) back into the pumping chamber. The valves 330 may include umbrella valves as shown, and the operating frequency may be between 20 Hz and 120 Hz (e.g., between 20 and 80 Hz, between 40 and 100 Hz, between 60 and 120 Hz, overlapping ranges thereof, or any value within the recited ranges). The valves 330 may include reed valves, ball check valves, and/or other check valves used in conjunction or in the alternative with umbrella valves.

Figures 1, 3C:
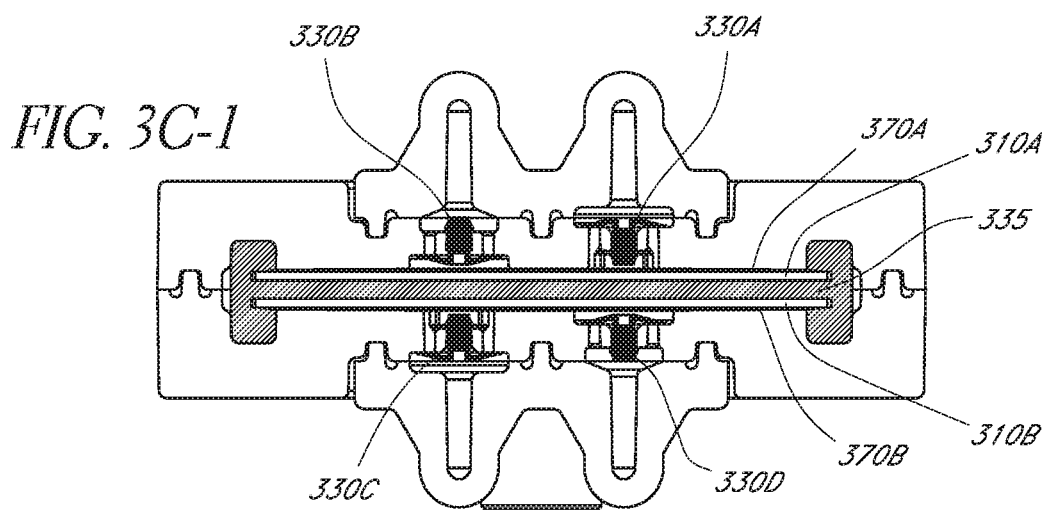
Figures 2, 3C:
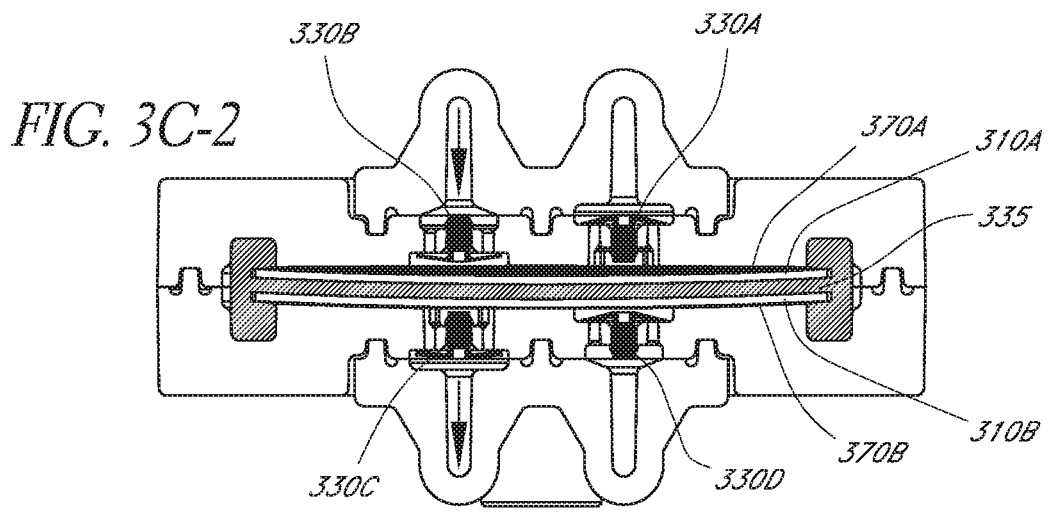
Figures 3, 3C:
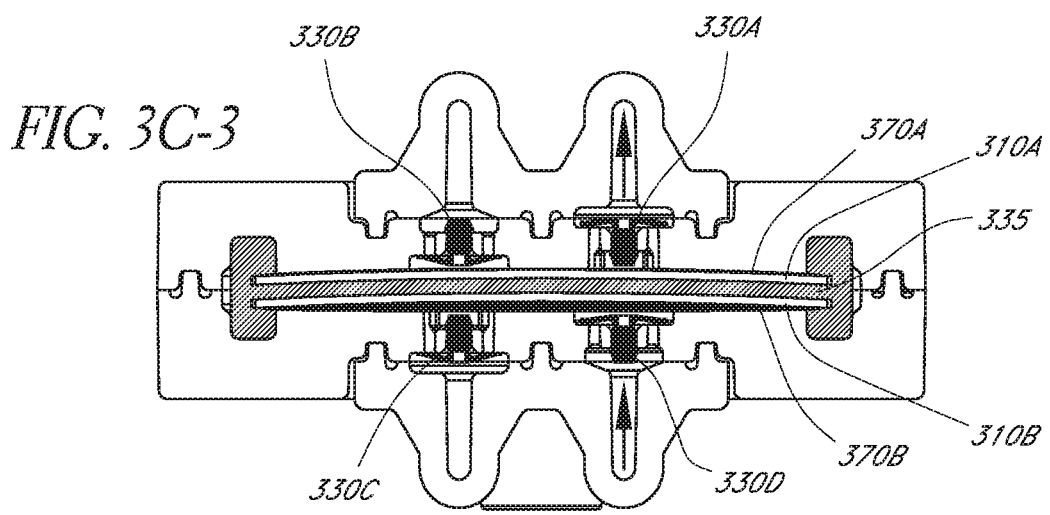

FIGS. 3C-1 to 3C-3 illustrate operation of the piezoelectric pump 300 in various configurations of the piezoelectric members 310. In FIG. 3C-1, the piezoelectric members 310 are in a neutral, non-energized configuration or state. The chambers or cavities 370A, 370B formed between the respective piezoelectric members 310 (e.g., discs, plates) and the inner surface of the respective housings 320, 325 match the size and shape of the maximum displacement of the piezoelectric members 310 when fully energized, thus minimizing any dead space within the chambers 370. Minimizing the dead space advantageously increases the efficiency of the pump 300, including the output pressure and flow rate. For each chamber 370, there is one exhaust port 330A, 330C and one inlet port 330B, 330D. In this neutral state, all of the valves 330 are closed and no fluid is being moved. In FIG. 3C-2, the piezoelectric members 310 are fully energized in one polarity and both piezoelectric members 310 are deflected toward the bottom housing 325. The bottom exhaust port 330C has a valve positioned to allow fluid (e.g., air) to flow out of the chamber 370B when the bottom piezoelectric member 310B deflects into the chamber 370B and the inlet port 330B replaces the fluid (e.g., air) in the chamber 370A while the top piezoelectric member 310A is not deflected into the chamber 370A. In FIG. 3C-3, the piezoelectric members 310 are fully energized in the opposite polarity and both piezoelectric members 310 are deflected toward the top housing 320. The exhaust port 330A has a valve positioned to allow fluid (e.g., air) to flow out of the chamber 370A when the top piezoelectric member 310A deflects into the chamber 370A and the inlet port 330D replaces the fluid (e.g., air) in the chamber 370B while the bottom piezoelectric member 310B is not deflected into the chamber 370B. The fluid ports 315 connected to each pump chamber 370 may be connected in parallel to increase the total fluid (e.g., air) flow provided by the pump 300.

The piezoelectric members 310 may comprise a stack of two or more piezoelectric discs (e.g., two, three, four, five, or more than five). In accordance with several embodiments, the stack of piezoelectric discs advantageously enables the piezoelectric members 310 to apply more force than could be applied from a single member (e.g., disc). The increased force may enable the pump 300 to generate more fluid (e.g., air) pressure and more fluid flow. For example, a single piezoelectric disc may deflect to a maximum amplitude of 0.75 mm and can apply approximately 15 N of force when energized with a 180V charge. By stacking two piezoelectric discs together, the piezoelectric members 310 may be able to provide approximately twice the force of one disc and the pump 300 may therefore be able to supply higher fluid pressure. In some embodiments, the piezoelectric members 310 may provide less or greater force depending on the material. For example, a single disc may provide less than 10 N of force in some embodiments. In other embodiments, a single piezoelectric disc may provide greater than 100 N of force, and a stack of piezoelectric discs forming a piezoelectric assembly may provide greater than 1000 N of force.

For operation with a NIBP monitor, it may be desirable to provide at least 6 psi of pressure. In some embodiments, this amount of force or pressure can be provided by the stacked piezoelectric members. In addition to the necessary force, sufficient air volume must also be provided. The deflection of the piezoelectric members (e.g., discs, plates) when driven may be small. For example, the maximum deflection for most ceramic materials may be approximately 0.30 to 0.75 mm. In some embodiments, the maximum deflection is smaller, such as in the range of 0.10 to 0.50 mm, or is larger such as from 0.75 up to 2.0 mm. Based on the relatively small deflection, depending on the size of the piezoelectric members (e.g., plates, discs) and other factors, the air volume provided through the outlet valves based on the deflection may be less than a milliliter per stroke. In addition to the degree of deflection generated by a given piezoelectric member, the volume of air provided per stroke depends on the size of the piezoelectric member. For example, a deflection of 0.75 mm by a disc with a surface area of approximately 125 $cm^2$ may provide a greater volume of air per stroke than a similar disc with a surface area of approximately 50 $cm^2$. For practical application with a NIBP monitor, it may be desirable to provide greater than 1 L/min of air flow. To increase air flow, the pump embodiment shown in FIGS. 3A-4B includes pump chambers 370 on each side of the piezoelectric assembly.

For a practical gas sample needed for a gas monitoring function, it is desirable to have suction of −20 to −300 mBar with a flow of 20-300 mL/hour, much smaller than required for the NIBP application. Again having two chambers 370 in parallel provides increased suction volume, while plumbing the two chambers 370 in series will provide increased suction pressure. The drive voltage of the stacked piezoelectric discs 310 may be configured such that the positive half wave deflects the discs into one chamber, while the negative half wave deflects the discs 310 into the other chamber. The outputs of the chambers when connected in parallel assures that air volume provided from the pump 300 is twice (or very close to twice) what would be provided by a single chamber. Should optimization of output pressure/suction be desired, the two chambers 370 may be connected in series. With the configuration shown in FIGS. 3A-4B, a desirable air flow greater than 50 to 300 mL/min may be attained by pumping at a rate in the range of thousands of strokes per minute, or approximately 80 Hz. In some embodiments, there may be less air flow per pump stroke and higher stroke rates (such as on the order of tens of thousands of strokes per minute) may be used to generate the required air flow per minute. In some embodiments, fewer strokes per minute may be required. For example, the pump 300 may generate more fluid (e.g., air) flow per stroke or the application may require a lower flow rate, depending upon the compressibility of the fluid and application requirements. In such embodiments, the pump 300 may operate in the range of hundreds of strokes per minute. In some embodiments with greater air flow requirements, the pump 300 may be operated at a range of 1,000-10,000 strokes per second.

As the piezoelectric plate 310 deflects into its chamber, the fluid (e.g., air, water) in the chamber is pressurized and begins to flow through one of the valves 330 and through the exhaust fluid port 315. The pumped fluid (e.g., air) may inflate a cuff for use with a NIBP monitoring device. Or likewise, if using the suction (inlet port), gas may be drawn from the patient's airway and through the gas analyzer for $CO_2$ and other gases of medical concern.

Figure 4A:
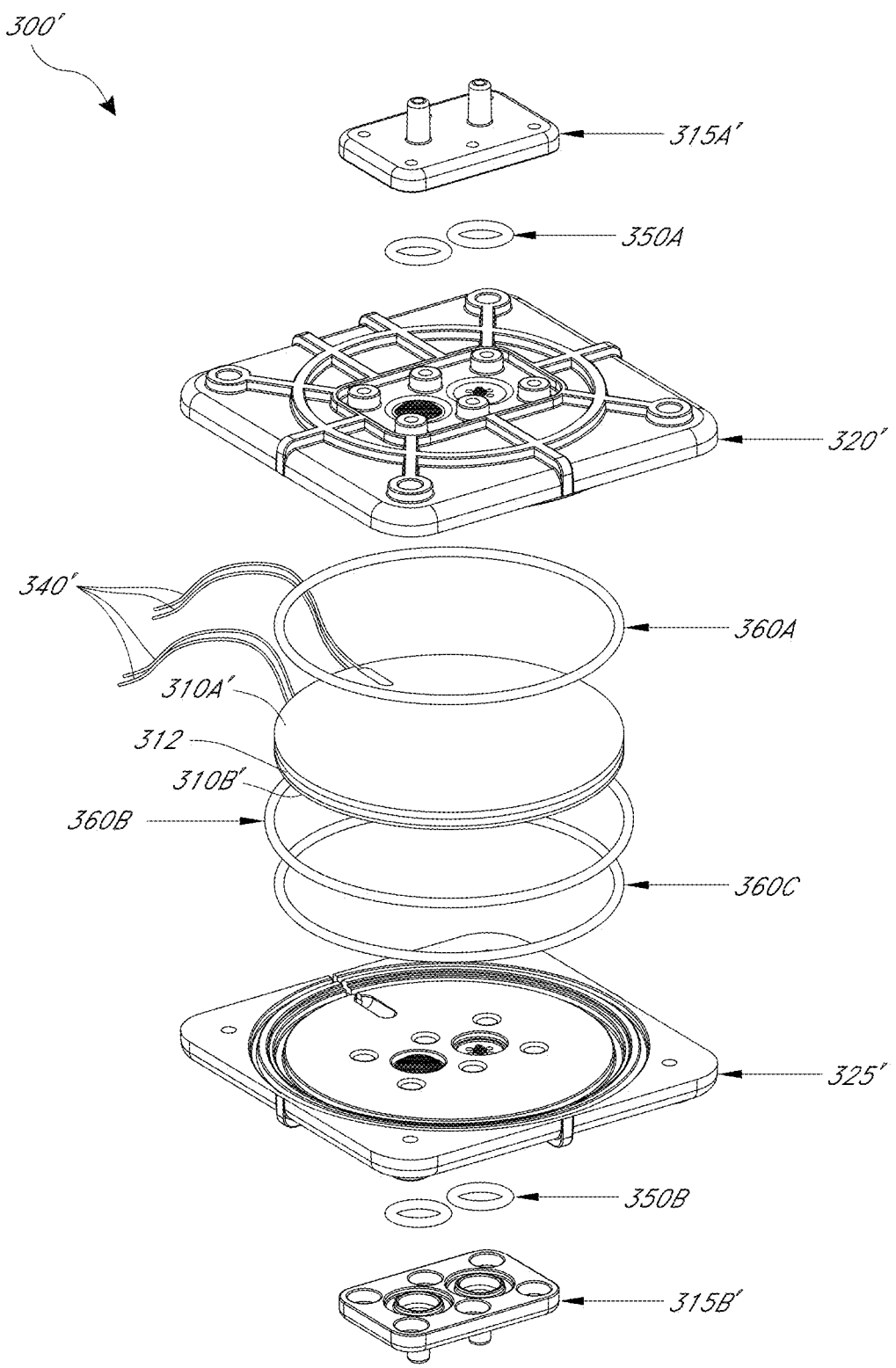
FIG. 4A is an exploded assembly view of an embodiment of a piezoelectric pump configured for safe and effective use in an MRI environment.
Figure 4B:
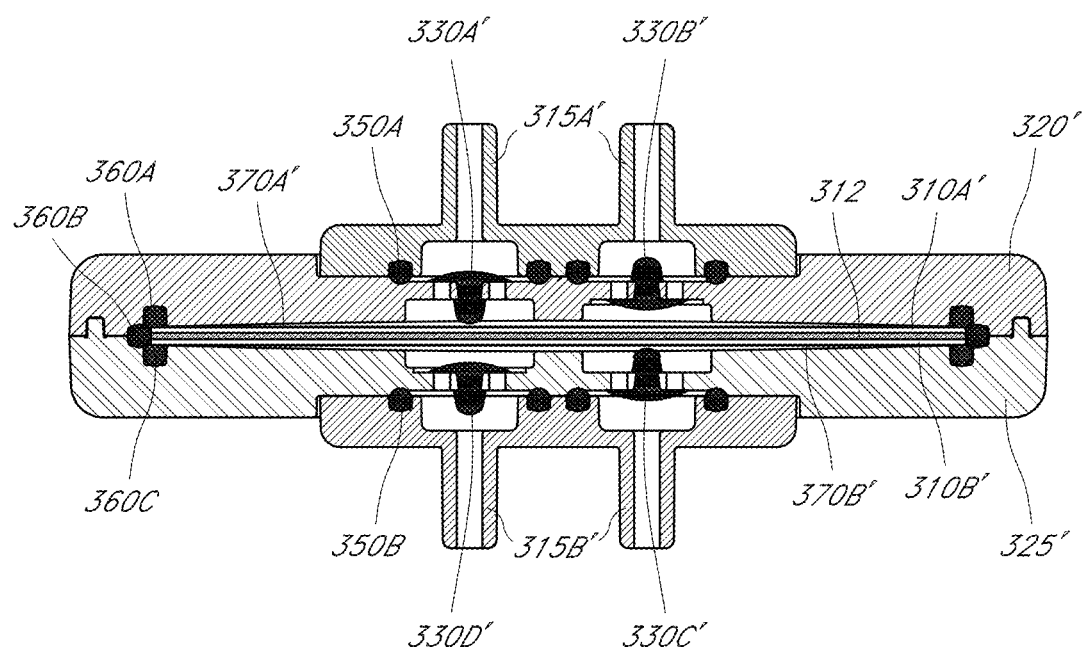
FIG. 4B is a cross-section view of the assembled piezoelectric pump of FIG. 4A.

FIGS. 4A and 4B illustrate another embodiment of a piezoelectric pump 300'. FIG. 4A is an exploded assembly view and FIG. 4B is a cross-section view of the piezoelectric pump 300'. Similar to the piezoelectric pump 300, the piezoelectric pump 300' includes multiple piezoelectric members 310', top fluid ports 315A', bottom fluid ports 315B', a top housing 320', a bottom housing 325', exhaust valves 330' and electrical leads 340'. The piezoelectric members 310' includes a piezoelectric assembly of two piezoelectric discs separated by a silicone rubber wafer 312. The piezoelectric pump 300' also includes multiple sealing members 350, 360 of various sizes to provide sealing in the connections between the fluid ports 315' and the housings 320', 325' and between the housings 320', 325' and the piezoelectric members 310'. The sealing members 350, 360 may be O-rings or other suitable resilient sealing gaskets. For example, in FIG. 4A, the pump 300' includes top, bottom, and center O-rings to seal the chambers formed by the assembled device. In some embodiments, one, some or all of the sealing members 350, 360 are replaced with adhesive. The piezoelectric assembly comprises one or more piezoelectric discs. In some embodiments, each piezoelectric member 310' consists of only one piezoelectric disc. However, each piezoelectric member 310' can include multiple stacked discs. The silicon rubber wafer 312 and/or sealing members 360 may provide support for the piezoelectric disc layers. In several embodiments, the O-rings 360 advantageously prevent fluid (e.g., air) from leaking from one chamber to another, leaking from a chamber to the outside of the pump 300, and from leaking out of the pump 300 instead of being directed through the fluid ports 320. In some embodiments fewer or additional O-rings 360 may be provided.

FIG. 4B illustrates the piezoelectric pump 300' when in the neutral, non-energized configuration or state. As shown both chambers 370A', 370B' are visible because neither of the piezoelectric members 310' is deflected and the valves 330' are all closed. The piezoelectric pump 300' may be configured to operate similar to the operation of the piezoelectric pump 300 as described above and will not be described again in further detail.

The configurations shown in FIGS. 3 and 4 illustrate two stacked piezoelectric discs or plates. In some embodiments, only one piezoelectric disc may be used or additional piezoelectric discs beyond two may be used. In some embodiments of a piezoelectric pump 300, 300', the pump may only have one chamber. For example, one or more discs may be driven so that they only deflect in one direction. In other embodiments, there may be additional pump chambers. For example, a pump may have multiple discs configured to each deflect into its own pump chamber. One approach, as shown, is to have 180° opposing pump chambers and drive the piezo actuators with a bipolar voltage, moving the actuators from fully deflected or distended into one chamber and then fully into the other. In some embodiments, the piezoelectric actuators are in a shape other than a disc. For example, the piezoelectric actuators may be rectangular, triangular, trapezoidal, rings, tubes or other shapes that allows the actuators to be positioned in a pump chamber.

FIG. 7 schematically illustrates drive electronics for the piezoelectric pumps 300, 300'. In accordance with several embodiments, the composite output drive voltage signal 701 generated by the drive electronics of FIG. 7 is sinusoidal or pseudo-sinusoidal in shape, as shown, for example, in FIG. 7A. The pseudo-sinusoidal shape may be generated using logic gates, as shown at the bottom of FIG. 7. In accordance with some embodiments, square wave drive can shorten the life of the ceramics, make control of the deflection suboptimal and so not fully minimize dead space at the peak of deflection, or allow the piezo ceramics to hit the inside of the chamber causing damage and noise. Pump flow can be controlled by either adjusting the drive frequency using frequency control 702 or voltage (HV) control 703, or a combination of both. In one embodiment, the drive circuitry 700 provides a 70 Hz, 120 Vpp output drive signal.

Ultrasonic Diaphragm Pumps

Turning to FIGS. 5A-5C, an embodiment of the non-magnetic ultrasonic motor (USM) driven pump 140 configured for use in an MRI environment is illustrated. In some embodiments, a NIBP monitor (e.g., the pump 140 in the blood pressure monitoring unit 101) may operate using an ultrasonic motor operably attached to a diaphragm air pump. The non-magnetic pump 140 may be configured to be driven by an ultrasonic motor (e.g., rotary ultrasonic motor) to facilitate non-invasive blood pressure monitoring within an MRI scan room (and even within a bore or imaging volume of an MRI imaging unit) while MRI imaging of a patient's body is being performed without detrimentally interfering with the images and without the operation of the pump 140 being detrimentally affected by operation of the MRI equipment. FIG. 5A is an exploded assembly view and FIG. 5B is a perspective view of the assembled pump 140. The illustrated embodiment of the pump 140 includes a pump housing 550, multiple heat sinks 555, a stator 560, a rotor 565 (the stator and rotor together form the motor), one or more shims 570, a drive shaft 575 and a rotor spring 577. Various components may be coupled together by fastening members (e.g., screws) as illustrated or by laser machining or welding or adhesives. FIG. 5C illustrates internal components of the pump housing 550. The pump mechanism of the pump 140 comprises a dual head diaphragm-type air pump that includes two diaphragms 580 on opposing sides of an eccentric cam 585. The pump 140 is an air pump that utilizes a rotary ultrasonic motor to drive the diaphragm pump mechanism to develop the pressure and flow necessary for use in the blood pressure monitoring unit 101 of the multi-parameter monitor 100.

The rotor spring 577 is mounted to an end (e.g., proximal end) of the drive shaft 575. The rotor spring 577 applies a specific pressure to the rotor/stator combination (e.g., motor). One or more shims 570 of various thickness are placed just under the rotor spring 577 to set the pressure at which the rotor 565 presses against the stator 560. In accordance with several embodiments, proper pressure is critical to achieving the proper speed/power profile of the motor. Generally, higher pressure allows greater torque, while lower pressure allows greater speed. The spring force and resultant rotor to stator pressure can be set for a non-load speed of 300-350 RPM. The spring force for a 45 mm diameter piezo stator will typically be from 6 to 10 kgf.

In accordance with one embodiment, the drive power for the motor of the non-magnetic pump 140 is a dual-phase sinusoidal power of approximately 44 kHz and 300 V pk-pk. A feedback signal may be used by the motor drive circuit (e.g., drive circuit 600 of FIG. 6) to stabilize the speed via control of the drive frequency as the stator temperature and shaft load change. Drive power to the stator 560 creates a traveling mechanical wave at its mating surface with the rotor 565, causing the rotor 565 to 'ride' the traveling wave and rotate.

The heat sinks 555 provide the requisite heat dissipation to prevent overheating of the motor caused by the significant friction between the stator 560 and the rotor 565. Due to the desired maximization of speed, there is a large amount of heat generated by friction between the rotor 565 and the stator 560. The stator 560 is coupled thermally to the heat sinks 555. The heat sinks 555 may consist of a single, monolithic component or a combination of multiple separate heat sinks (e.g., a disc and a plate as best shown in FIG. 5A). The heat sinks 555 may be formed of any material configured to conduct heat away from the stator 560. In some embodiments, one or more of the heat sinks 555 is further heat sunk by thermally affixing it to a larger thermally conductive surface within a housing of the monitor 100. Without proper removal of the heat, the mating surfaces of the rotor 565 and the stator 560 will rapidly wear, which can result in changing the spacing of the rotor spring 577 and lead to loss of pressure between the rotor 565 and stator 560, causing torque to fall to zero and the motor to cease rotation.

With reference to FIG. 5C, the drive bearing includes an eccentric cam or hole 585. The drive shaft 575 fits into the eccentric cam 585 and acts as the crank shaft for the two opposing diaphragms 580. As shown in the two bottom figures of FIG. 5C, the one diaphragm is compressed and pushing out air while the other is relaxed. As illustrated in FIG. 5C, the diaphragm pump may contain two chambers to generate air flow on both an up and a down stroke. In other embodiments, the diaphragm pump may only include one chamber and one exhaust port.

The diaphragms 580 may be formed and tensioned to minimize energy loss due to stretching the diaphragm material. An elastomer is a suitable material for the diaphragm and molding in a rolling outer edge shape minimizes energy wasted in stretching the diaphragm as it reaches the limits of its stroke. In addition the stroke distance of the piston rods, which are connected to the diaphragms 580, may be optimized to match the operation of the ultrasonic motor. Stroke is controlled by selection of the eccentric offset. In embodiments in which the diaphragms 580 are approximately 1 inch in diameter, a suitable eccentric offset is between 0.040 and 0.090 inch.

Figure 6:
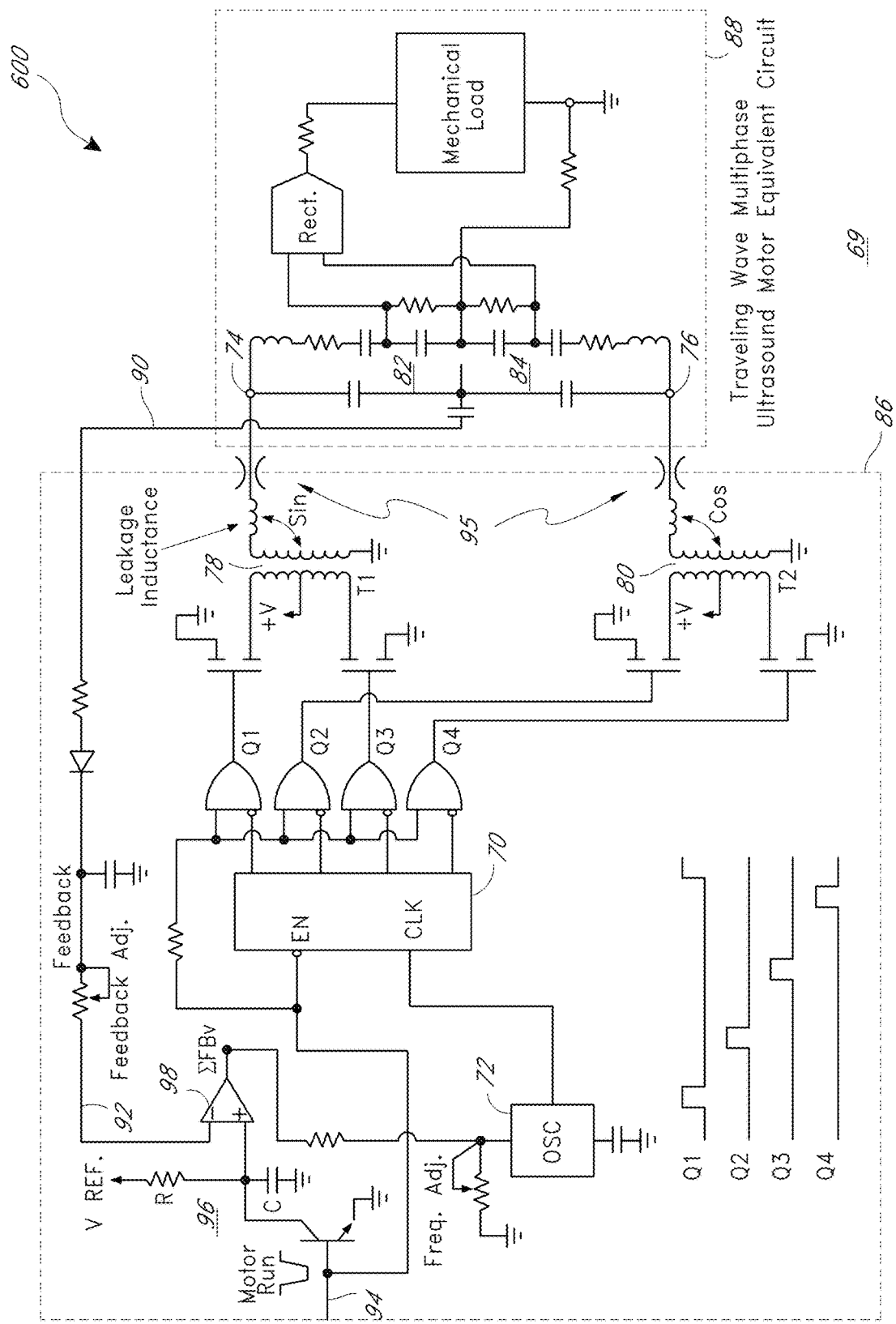
FIG. 6 is a schematic circuit diagram of drive electronics, or drive circuitry, for the ultrasonic motor driven non-magnetic pump of FIGS. 5A-5C.

The ultrasonic pump 140 may be driven by the circuit 600 illustrated in FIG. 6. As shown in FIG. 5A, the motor receives electrical signals via electrical leads 590. As illustrated, the leads may include a ground lead (GND), a feedback lead (F.B.), a sine lead (SIN) and a cosine lead (COS). The ultrasonic motor may be driven by a multiphasic electronic signal with little (e.g., an amount insufficient to cause any appreciable effect) RF harmonic noise in the spectral range of about 6 or 8 MHz to about 130 MHz in which MRI receivers are most sensitive. In some embodiments, the drive power for the ultrasonic motor is generated via circuitry which produces multiphasic drive signals of at least sine and cosine waveforms at related ultrasonic frequencies of approximately 40-46 kHz and 90 V to 110 $V_{rms}$ or approximately 300 V pk-pk. These drive signals may advantageously be produced as a sinusoidal wave to reduce high frequency harmonic components which may disturb RF responsiveness.

With continued reference to FIG. 6, one scheme for producing multiphasic signals uses coreless or "Air Core" transformers 78, 80 constructed with inherent leakage inductance that interacts with the complex impedance of the ultrasonic motor 88 (e.g., ultrasonic rotor/stator motor of FIGS. 5A-5C) to convert lower voltage square wave signals at the primary winding (V+ of FIG. 6) into sinusoidal high voltage signals at the secondary windings 74, 76 suitable for powering the ultrasonic motor and producing little harmonic RF interference. Alternatively, D.C. voltages of opposite polarities can be alternately switched to supply alternating voltages. The switched signals can be filtered into sinusoidal signals and applied to the inputs of high voltage linear amplifiers that are set for such gain as needed to produce resultant outputs of sufficient voltage and sinusoidal shape to drive the ultrasonic motor.

Still another method may be to use linear or switching amplifiers powered from a high voltage supply rail, to amplify a sin and cos ultrasonic motor drive signal to the proper voltage level. The low level sin and cos drive signal generated either by an oscillator or digitally via software and digital-to-analog conversion (DAC) devices or techniques. The illustrated embodiment in FIGS. 5A-5C and 6 uses a two-phase ultrasonic motor with a feedback signal 90 corresponding to the motor's loaded speed. The feedback loop can be used to regulate startup frequency as well as stabilize speed variations due to load changes. An RC network 96 is summed at feedback summing amp 98 with the motor feedback signal to generate a summed feedback voltage, ΣFBv. At startup, before the ultrasonic motor has actually begun to turn, signal 92 is null and so the ramping signal, as the RC network 96 charges, is the significant ΣFBv from feedback summing amp 98 into oscillator 72. This ramping feedback signal is such that the oscillator frequency is swept over a narrow range from high to lower frequency (e.g., 46 kHz to 44 kHz). The frequency sweep range for a noninvasive blood pressure air pump may have a maximum of 5 kHz while the typical running frequency for the ultrasonic NIBP air pump motor may be 44 kHz, in accordance with several embodiments.

Figure 6A:
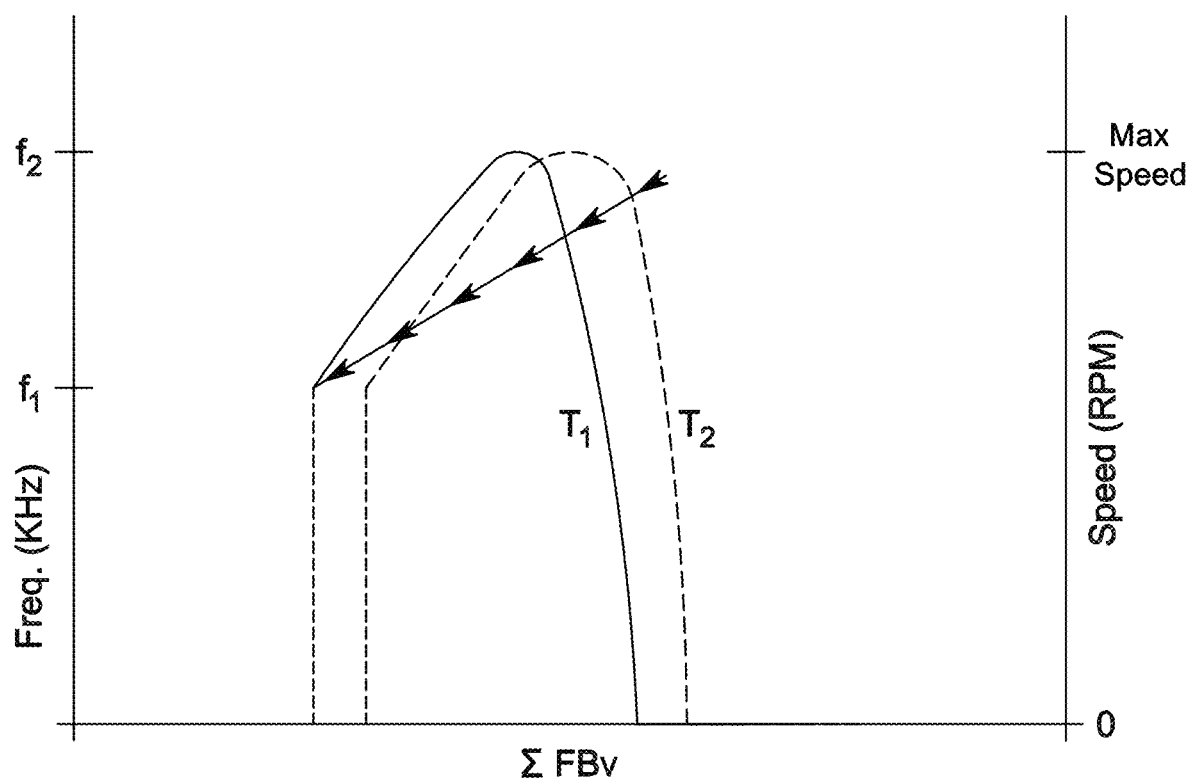
FIG. 6A is graph illustrating a frequency sweep range of the drive power to the ultrasonic motor driven pump of FIGS. 5A-5C using feedback control to maintain motor speed and sweep the operating frequency for the ultrasonic motor start.

The need for starting the oscillator 72 at an upper frequency and sweeping to lower frequency is to allow the ultrasonic motor drive frequency to sweep into a frequency at which the motor will start and then reach its desired operating speed. The piezo-ceramic material which forms the stator 560 (e.g., 45 mm stator) of the ultrasonic motor is resonant at approximately 44 kHz; however, this varies with temperature and somewhat with load. Until driven very near resonance, the motor will not run. The graph of FIG. 6A shows the relationship of the frequency to the motor speed as controlled by the summed feedback from the feedback summing amplifier 98. The two speeds plotted on the graph represent the startup and speed profile of an ultrasonic motor at two temperatures, T1 and T2. When the motor run signal 94 is applied, the RC network 96 begins charging, producing a positive ramp through the feedback summing amplifier 98 which causes the voltage-controlled oscillator 72 frequency to move from its nominal higher frequency to lower frequencies. As the ultrasonic motor (e.g., rotor 565) begins to turn it produces the feedback signal 90 and adjustable feedback control 92, summed at feedback summing amplifier 98, which counteracts the ramping effect at the RC network 96 and holds the oscillator frequency associated with the Feedback Adjustment setting, yielding the desired motor running speed (e.g., at or about 300 RPM). The amount of negative feedback set at adjustable feedback control 92 determines the running speed which can range from 10 RPM to the maximum capability of the ultrasonic motor (e.g., rotor 565), which is approximately 400 RPM with a spring force 577 of 8.5 kgf.

Additional Language

In accordance with several embodiments, no magnetic material is used in any of the components of the pumps 140, 300, 300' described herein, including the motors, diaphragms, power supplies, control or drive circuitry, and other associated components. Additionally, none of such components is adversely affected during operation by a strong magnetic field. Any RF energy that may be generated by electronic signals within the pumps, control circuitry 105, power supply 110 or associated components may specifically be shielded by conductive structures disposed around such components to inhibit radiation of radio frequency interference. Additionally, radio-frequency interference filters may be disposed about all through-shield conductors to inhibit radiation of RFI through such portals.

The non-magnetic pumps disclosed above may have additional applications. For example, the pumps may be used to pump fluids for other purposes in an MRI environment, such as liquids used for heating or cooling of the patient. The pumps may also be used in other environments which do not have the same non-magnetic and RF requirements, but may otherwise take advantage of the characteristics of the pumps. For example, the piezoelectric pump may be used in areas that require motors that produce very little audio or RF noise (for example, IV pumps, automotive fluids, flammable fluids, or aquariums or fish tanks).

While certain embodiments of the disclosure have been described, these embodiments have been presented by way of example only, and are not intended to limit the scope of the disclosure. Indeed, the novel methods, systems, and devices described herein may be embodied in a variety of other forms. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Furthermore, various omissions, substitutions and changes in the form of the methods, systems, and devices described herein may be made without departing from the spirit of the disclosure.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 300 RPM" includes "300 RPM."

What is claimed is:

1. A non-magnetic displacement pump comprising:
   a pump housing forming a pump chamber within the pump housing,
   wherein the pump housing comprises an upper housing and a lower housing attached to form the pump housing;
   a piezoelectric plate assembly positioned within the pump chamber between the upper housing and the lower housing, the piezoelectric plate assembly comprising:
      a first piezoelectric disc;
      a second piezoelectric disc; and
      an elastomeric carrier comprising a first side and a second side;
      wherein the first piezoelectric disc is positioned on the first side of the elastomeric carrier within the upper housing;
      wherein the second piezoelectric disc is positioned on the second side of the elastomeric carrier within the lower housing; and
      wherein the elastomeric carrier has an insulation member between the first side and the second side to electrically insulate the first piezoelectric disc from the second piezoelectric disc,
      wherein a space between the first piezoelectric disc and the upper housing forms an upper chamber of the pump chamber and a space between the second piezoelectric disc and the lower housing forms a lower chamber of the pump chamber;
   a first exhaust port operably connected to the upper chamber;
   a first valve positioned between the upper chamber and the first exhaust port;
   a second exhaust port operably connected to the lower chamber;
   a second valve positioned between the lower chamber and the second exhaust port;
   a first inlet port operably connected to the upper chamber;
   a third valve positioned between the upper chamber and the first inlet port;
   a second inlet port operably connected to the lower chamber;
   a fourth valve positioned between the lower chamber and the second inlet port;
   a drive circuit configured to energize the first and second piezoelectric discs;
   wherein the first piezoelectric disc and the second piezoelectric disc are operably connected to the drive circuit such that:
      the first and second piezoelectric discs deflect toward the upper housing when positive voltage is applied by the drive circuit; and
      the first and second piezoelectric discs deflect toward the lower housing when negative voltage is applied by the drive circuit,
   wherein the upper chamber is formed in a shape substantially similar to a contour of the first piezoelectric disc when the positive voltage is applied by the drive circuit so as to minimize an amount of dead space in the upper chamber due to displacement of the first piezoelectric disc when the positive voltage is applied, thereby increasing output volume through the first exhaust port, wherein the lower chamber is formed in a shape substantially similar to a contour of the second piezoelectric disc when the negative voltage is applied by the drive circuit so as to minimize an amount of dead space in the lower chamber due to displacement of the second piezoelectric disc when the negative voltage is applied, thereby increasing output volume through the second exhaust port;

wherein the pump is configured to pump air at a flow rate of 50 mL/min to 300 mL/min, and wherein the pump is configured to operate at a frequency between 20 Hz and 240 Hz.

2. The non-magnetic pump of claim 1, wherein the drive circuit is configured to energize the first and second piezoelectric discs with a sinusoidal or pseudo-sinusoidal wave.

3. The non-magnetic pump of claim 2, wherein the wave is in a range of 20 to 180 volts peak to peak.

4. The non-magnetic pump of claim 3, wherein the wave has a frequency between 20 Hz and 100 Hz.

5. The non-magnetic pump of claim 1, wherein the upper housing and the lower housing are made of a non-magnetic material.

6. The non-magnetic pump of claim 1, wherein the pump is configured for use within a gas analyzer unit.

7. A non-magnetic displacement pump comprising:
a pump housing forming a pump chamber within the pump housing,
wherein the pump housing comprises an upper housing and a lower housing;
a first piezoelectric disc positioned within the upper housing;
a second piezoelectric disc positioned within the lower housing;
an insulation member positioned between the first piezoelectric disc and the second piezoelectric disc,
wherein a space between the first piezoelectric disc and the upper housing forms an upper chamber of the pump chamber and a space between the second piezoelectric disc and the lower housing forms a lower chamber of the pump chamber; a first exhaust port operably connected to the upper chamber; a second exhaust port operably connected to the lower chamber; a first inlet port operably connected to the upper chamber; a second inlet port operably connected to the lower chamber;
a drive circuit configured to energize the first and second piezoelectric discs;
wherein the first piezoelectric disc and the second piezoelectric disc are operably connected to the drive circuit such that:
the first and second piezoelectric discs and the insulation member deflect toward the upper housing when positive voltage is applied by the drive circuit; and
the first and second piezoelectric discs and the insulation member deflect toward the lower housing when negative voltage is applied by the drive circuit, wherein the upper chamber is formed in a shape substantially similar to a profile of the first piezoelectric disc when the positive voltage is applied by the drive circuit so as to minimize an amount of dead space in the upper chamber due to displacement of the first piezoelectric disc when the positive voltage is applied, wherein the lower chamber is formed in a shape substantially similar to a profile of the second piezoelectric disc when the negative voltage is applied by the drive circuit so as to minimize an amount of dead space in the lower chamber due to displacement of the second piezoelectric disc when the negative voltage is applied;

wherein the pump is configured to pump air at a flow rate of 50 mL/min to 300 mL/min, and wherein the pump is configured to operate at a frequency between 20 Hz and 240 Hz.

8. The non-magnetic pump of claim 7, further comprising:
an elastomeric carrier comprising a first side and a second side;
wherein the first piezoelectric disc is positioned in a first recess on the first side of the elastomeric carrier;
wherein the second piezoelectric disc is positioned in a second recess on the second side of the elastomeric carrier.

9. The non-magnetic pump of claim 7, wherein the drive circuit is configured to energize the first and second piezoelectric discs with a sinusoidal or pseudo-sinusoidal wave.

10. The non-magnetic pump of claim 9, wherein the wave is in a range of 20 to 180 volts peak to peak.

11. The non-magnetic pump of claim 10, wherein the wave has a frequency between 20 Hz and 100 Hz.

12. The non-magnetic pump of claim 7, further comprising:
a first valve positioned between the upper chamber and the first exhaust port;
a second valve positioned between the lower chamber and the second exhaust port;
a third valve positioned between the upper chamber and the first inlet port; and
a fourth valve positioned between the lower chamber and the second inlet port.

13. The non-magnetic pump of claim 7, wherein the upper housing and the lower housing are made of a non-magnetic material.

14. The non-magnetic pump of claim 7, wherein the pump is configured for use within a gas analyzer unit.

* * * * *